(12) United States Patent
Engh et al.

(10) Patent No.: US 7,115,131 B2
(45) Date of Patent: Oct. 3, 2006

(54) APPARATUS AND METHOD FOR SCULPTING THE SURFACE OF A JOINT

(75) Inventors: Gerard A. Engh, Alexandria, VA (US); Wesley D. Johnson, Eden Prairie, MN (US)

(73) Assignee: Alexandria Research Technologies, LLC, Plymounth, MN (US)

( * ) Notice: Subject to any disclaimer, the term of this patent is extended or adjusted under 35 U.S.C. 154(b) by 0 days.

(21) Appl. No.: 10/159,147

(22) Filed: May 29, 2002

(65) Prior Publication Data

US 2002/0198528 A1    Dec. 26, 2002

Related U.S. Application Data

(62) Division of application No. 09/882,591, filed on Jun. 14, 2001, now Pat. No. 6,482,209.

(51) Int. Cl.
*A61B 17/00* (2006.01)
*A61F 2/38* (2006.01)

(52) U.S. Cl. ............ 606/79; 623/20.21; 623/20.3; 623/20.31

(58) Field of Classification Search .......... 606/79, 606/80, 82, 86, 88; 623/20.11, 20.14, 20.15, 623/20.21, 20.3, 20.31, 20.32, 20.34, 20.35, 623/20.33, 20.29, 20.23, 20.16, 16.11, 13.12, 623/18.11, 20.18, 20.19, 20.2
See application file for complete search history.

(56) References Cited

U.S. PATENT DOCUMENTS

| | | | |
|---|---|---|---|
| 2,179,250 A | 11/1939 | D'Amato | |
| 3,852,830 A | 12/1974 | Marmor | |
| 3,869,731 A * | 3/1975 | Waugh et al. | 623/20.21 |
| 3,949,428 A | 4/1976 | Cavendish et al. | |
| 3,953,899 A | 5/1976 | Charnley | |
| 4,034,418 A * | 7/1977 | Jackson et al. | 623/20.3 |
| 4,207,627 A * | 6/1980 | Cloutier | 623/20.21 |
| 4,209,861 A | 7/1980 | Walker et al. | |
| 4,216,549 A | 8/1980 | Hillberry et al. | |
| 4,224,696 A | 9/1980 | Murray et al. | |
| 4,261,064 A * | 4/1981 | Helfet | 623/20.31 |
| 4,340,978 A | 7/1982 | Buechel et al. | |
| 4,457,307 A | 7/1984 | Stillwell | |

(Continued)

FOREIGN PATENT DOCUMENTS

DE    3013155 A1    10/1980

(Continued)

OTHER PUBLICATIONS

"Subvastus Approach for Total Knee Arthroplasty: A Prospective, Randomized, and Observer-Blinded Trial." G.S. Roysam, FRCS (orth) and M.J. Oakley, FRCS. The Journal of Arthroplasty. vol. 16, No. 4 2001. Churchill Livingstone 2001.

(Continued)

*Primary Examiner*—Pedro Philogene
(74) *Attorney, Agent, or Firm*—Barbara A. Wrigley; Oppenheimer Wolff & Donnelly LLP

(57) ABSTRACT

The present invention provides a method and device for restoring individual patient joint kinematics using minimally invasive surgical procedures. The instrumentation of the invention sculpts the articular surface of a first bone that normally articulates in a predetermined manner with a second bone. The instrumentation includes a bone sculpting tool and a mount for attaching the tool to the second bone. The implant system is comprised of implants that provide intraoperative surgical options for articular constraint and facilitate proper alignment and orientation of the joint to restore kinematics as defined by the individual patient anatomy.

78 Claims, 14 Drawing Sheets

U.S. PATENT DOCUMENTS

| | | | |
|---|---|---|---|
| 4,487,203 A | 12/1984 | Androphy | 128/303 |
| 4,524,766 A | 6/1985 | Petersen | 128/92 |
| 4,567,885 A | 2/1986 | Androphy | 128/92 |
| 4,568,348 A | 2/1986 | Johnson et al. | |
| 4,574,794 A | 3/1986 | Cooke et al. | |
| 4,586,933 A | 5/1986 | Shoji et al. | |
| 4,714,474 A | 12/1987 | Brooks, Jr. et al. | 623/20 |
| 4,728,332 A * | 3/1988 | Albrektsson | 623/20.29 |
| 4,759,350 A | 7/1988 | Dunn et al. | 128/92 |
| 4,770,663 A | 9/1988 | Hanslik et al. | |
| 4,822,366 A | 4/1989 | Bolesky | |
| 4,865,606 A * | 9/1989 | Rehder | 623/20.23 |
| 4,911,721 A * | 3/1990 | Andergaten et al. | 623/20.3 |
| 4,938,762 A | 7/1990 | Wehrli | 606/88 |
| 4,944,760 A | 7/1990 | Kenna | 623/20 |
| 5,037,423 A | 8/1991 | Kenna | 606/88 |
| 5,092,895 A | 3/1992 | Albrektsson et al. | |
| 5,100,409 A | 3/1992 | Coates et al. | |
| 5,116,375 A | 5/1992 | Hofmann | |
| 5,123,927 A | 6/1992 | Duncan et al. | |
| 5,133,760 A | 7/1992 | Petersen et al. | |
| 5,135,760 A | 8/1992 | Degady et al. | |
| 5,147,406 A | 9/1992 | Houston et al. | |
| 5,152,796 A | 10/1992 | Slamin | |
| 5,158,342 A | 10/1992 | Pai | |
| D331,461 S | 12/1992 | Lester | D24/140 |
| 5,171,244 A * | 12/1992 | Caspari et al. | 606/88 |
| 5,171,282 A * | 12/1992 | Pequignot | 623/20.35 |
| 5,181,925 A | 1/1993 | Houston et al. | |
| 5,219,362 A | 6/1993 | Tuke et al. | |
| D337,639 S | 7/1993 | Beckman | D24/133 |
| 5,226,916 A | 7/1993 | Goodfellow et al. | |
| 5,228,459 A | 7/1993 | Caspari et al. | |
| 5,234,433 A | 8/1993 | Bert et al. | 606/88 |
| 5,250,050 A | 10/1993 | Poggie et al. | 606/79 |
| 5,263,498 A | 11/1993 | Caspari et al. | 128/898 |
| 5,282,866 A | 2/1994 | Cohen et al. | |
| 5,282,868 A * | 2/1994 | Bahler | 623/20.29 |
| 5,326,359 A | 7/1994 | Oudard | |
| 5,358,527 A * | 10/1994 | Forte | 623/20.27 |
| 5,358,529 A | 10/1994 | Davidson | |
| 5,358,530 A * | 10/1994 | Hodorek | 623/20.29 |
| 5,358,531 A | 10/1994 | Goodfellow et al. | |
| 5,370,699 A | 12/1994 | Hood et al. | |
| 5,405,395 A | 4/1995 | Coates | |
| 5,405,398 A | 4/1995 | Buford, III et al. | |
| 5,413,604 A | 5/1995 | Hodge | |
| 5,417,693 A | 5/1995 | Sowden et al. | 606/85 |
| 5,417,695 A | 5/1995 | Axelson, Jr. | 606/89 |
| 5,423,822 A | 6/1995 | Hershberger et al. | 606/79 |
| 5,486,178 A | 1/1996 | Hodge | 606/82 |
| 5,496,324 A | 3/1996 | Barnes | |
| 5,540,696 A | 7/1996 | Booth, Jr. et al. | 606/88 |
| 5,549,684 A | 8/1996 | Amino et al. | |
| 5,549,685 A | 8/1996 | Hayes | |
| 5,549,688 A | 8/1996 | Ries et al. | |
| 5,569,255 A | 10/1996 | Burke | 606/79 |
| 5,569,259 A | 10/1996 | Ferrante et al. | |
| 5,575,793 A | 11/1996 | Carls et al. | 606/80 |
| 5,578,039 A | 11/1996 | Vendrely et al. | 606/88 |
| 5,609,639 A | 3/1997 | Walker | |
| 5,609,642 A | 3/1997 | Johnson et al. | 623/20 |
| 5,624,443 A | 4/1997 | Burke | 606/86 |
| 5,658,292 A | 8/1997 | Axelson, Jr. | 606/86 |
| 5,658,342 A | 8/1997 | Draganich et al. | |
| 5,667,511 A | 9/1997 | Vendrely et al. | 606/88 |
| 5,669,914 A | 9/1997 | Eckhoff | 606/88 |
| 5,683,468 A * | 11/1997 | Pappas | 623/20.29 |
| 5,683,469 A | 11/1997 | Johnson et al. | 623/20 |
| 5,683,470 A | 11/1997 | Johnson et al. | 623/20 |
| 5,688,280 A | 11/1997 | Booth, Jr. et al. | 606/88 |
| 5,690,636 A | 11/1997 | Wildgoose et al. | 606/88 |
| 5,690,638 A | 11/1997 | Dance et al. | 606/88 |
| 5,693,056 A | 12/1997 | Carls et al. | 606/86 |
| 5,702,466 A | 12/1997 | Pappas et al. | |
| 5,716,360 A | 2/1998 | Baldwin et al. | 606/80 |
| 5,725,584 A | 3/1998 | Walker et al. | |
| 5,725,596 A | 3/1998 | Burke | 623/23 |
| 5,728,162 A | 3/1998 | Eckhoff | |
| 5,741,264 A | 4/1998 | Cipolletti | 606/85 |
| 5,755,800 A | 5/1998 | O'Neil et al. | |
| 5,755,803 A | 5/1998 | Haines et al. | |
| 5,766,255 A | 6/1998 | Slamin et al. | |
| 5,769,854 A | 6/1998 | Bastian et al. | 606/88 |
| 5,769,855 A | 6/1998 | Bertin et al. | |
| 5,776,200 A | 7/1998 | Johnson et al. | 623/20 |
| 5,776,201 A | 7/1998 | Colleran et al. | |
| 5,782,925 A | 7/1998 | Callazo et al. | |
| 5,788,701 A | 8/1998 | McCue | 606/88 |
| 5,795,353 A | 8/1998 | Felt | 623/18 |
| 5,800,438 A | 9/1998 | Tuke et al. | 606/90 |
| 5,810,830 A | 9/1998 | Noble et al. | 606/85 |
| 5,824,098 A | 10/1998 | Stein | 623/20 |
| 5,824,104 A | 10/1998 | Tuke | 623/20 |
| 5,824,105 A | 10/1998 | Ries et al. | |
| 5,830,216 A | 11/1998 | Insall et al. | 606/88 |
| 5,851,183 A | 12/1998 | Bucholz | 600/425 |
| 5,853,415 A | 12/1998 | Bertin et al. | |
| 5,871,541 A | 2/1999 | Gerber | |
| 5,871,545 A | 2/1999 | Goodfellow et al. | |
| 5,879,354 A * | 3/1999 | Haines et al. | 606/86 |
| 5,880,976 A | 3/1999 | DiGioia, III et al. | 364/578 |
| 5,885,299 A | 3/1999 | Winslow et al. | 606/99 |
| 5,891,034 A | 4/1999 | Bucholz | 600/426 |
| 5,906,643 A | 5/1999 | Walker | |
| 5,925,049 A | 7/1999 | Gustilo et al. | 606/82 |
| 5,951,564 A | 9/1999 | Schroder et al. | 606/100 |
| 5,951,606 A | 9/1999 | Burke | 623/23 |
| 5,964,808 A | 10/1999 | Blaha et al. | |
| 5,976,147 A | 11/1999 | LaSalle et al. | 606/88 |
| 5,989,261 A | 11/1999 | Walker et al. | 606/102 |
| 5,997,543 A | 12/1999 | Truscott | 606/86 |
| 6,002,859 A | 12/1999 | DiGioia, III et al. | 395/500.32 |
| 6,010,509 A | 1/2000 | Delgado et al. | 606/88 |
| 6,013,079 A | 1/2000 | Salam | |
| 6,013,081 A | 1/2000 | Burkinshaw et al. | 606/88 |
| 6,013,103 A | 1/2000 | Kaufman et al. | |
| 6,018,094 A | 1/2000 | Fox | 623/11 |
| 6,056,756 A | 5/2000 | Eng et al. | 606/87 |
| 6,056,777 A * | 5/2000 | McDowell | 623/18.11 |
| 6,059,831 A * | 5/2000 | Braslow et al. | 128/898 |
| 6,063,091 A | 5/2000 | Lombardo et al. | 606/88 |
| 6,083,228 A | 7/2000 | Michelson | |
| 6,090,114 A | 7/2000 | Matsuno et al. | 606/88 |
| 6,096,043 A | 8/2000 | Techiera et al. | 606/88 |
| 6,106,529 A | 8/2000 | Techiera | 606/88 |
| 6,123,729 A | 9/2000 | Insall et al. | |
| 6,126,693 A | 10/2000 | O'Neil et al. | |
| 6,132,468 A | 10/2000 | Mansmann | 623/20.16 |
| 6,146,390 A | 11/2000 | Heilbrun et al. | 606/130 |
| 6,159,214 A | 12/2000 | Michelson | 606/80 |
| 6,165,181 A | 12/2000 | Heilbrun et al. | 606/130 |
| 6,165,221 A * | 12/2000 | Schmotzer | 623/20.11 |
| 6,165,223 A | 12/2000 | Metzger et al. | |
| 6,168,629 B1 | 1/2001 | Timoteo | |
| 6,171,340 B1 * | 1/2001 | McDowell | 623/18.11 |
| 6,179,877 B1 | 1/2001 | Burke | 623/22.12 |
| 6,190,415 B1 | 2/2001 | Cooke et al. | |
| 6,197,064 B1 | 3/2001 | Haines et al. | 623/20.31 |
| 6,201,984 B1 | 3/2001 | Funda et al. | 600/407 |
| 6,206,927 B1 | 3/2001 | Fell et al. | 623/20.29 |
| 6,214,051 B1 | 4/2001 | Badorf et al. | |
| 6,214,052 B1 | 4/2001 | Burkinshaw | |
| 6,214,952 B1 | 4/2001 | Sadatoshi et al. | |

| | | | |
|---|---|---|---|
| 6,231,611 B1 | 5/2001 | Mosseri | |
| 6,235,060 B1 | 5/2001 | Kubein-Meesenburg et al. | |
| 6,236,875 B1 | 5/2001 | Bucholz et al. | 600/407 |
| 6,245,110 B1 | 6/2001 | Grundei et al. | |
| RE37,277 E | 7/2001 | Baldwin et al. | 623/20 |
| 6,283,980 B1 | 9/2001 | Vibe-Hansen et al. | 606/151 |
| 6,290,704 B1 | 9/2001 | Burkinshaw et al. | 606/88 |
| 6,299,645 B1 * | 10/2001 | Ogden | 623/20.21 |
| 6,332,780 B1 | 12/2001 | Traxel et al. | 434/267 |
| 6,342,075 B1 * | 1/2002 | MacArthur | 623/20.14 |
| 6,364,911 B1 | 4/2002 | Schmotzer et al. | |
| 6,379,367 B1 | 4/2002 | Vibe-Hansen et al. | 606/151 |
| 6,383,222 B1 | 5/2002 | Badorf | |
| 6,494,914 B1 * | 12/2002 | Brown et al. | 623/20.3 |
| 6,589,283 B1 | 7/2003 | Metzger et al. | |
| 6,702,821 B1 | 3/2004 | Bonutti | |
| 6,726,723 B1 | 4/2004 | Running | |
| 6,749,638 B1 | 6/2004 | Saladino | |
| 6,783,548 B1 | 8/2004 | Hyde, Jr. | |
| 2001/0012967 A1 | 8/2001 | Mosseri | 623/23.12 |
| 2001/0016778 A1 | 8/2001 | Badorf et al. | |
| 2002/0138150 A1 | 9/2002 | Leclercq | |
| 2002/0198528 A1 | 12/2002 | Engh et al. | |
| 2003/0153977 A1 | 8/2003 | Suguro et al. | |
| 2003/0158606 A1 | 8/2003 | Coon et al. | |
| 2003/0220697 A1 | 11/2003 | Justin et al. | |
| 2003/0225458 A1 | 12/2003 | Donkers et al. | |
| 2004/0102852 A1 | 5/2004 | Johnson et al. | |

FOREIGN PATENT DOCUMENTS

| | | | | |
|---|---|---|---|---|
| DE | 3305237 A1 | 8/1983 | | |
| DE | 19716879 A1 | 11/1998 | | |
| DE | 69528655 T2 | 7/2003 | | |
| EP | 0021421 | 6/1980 | | |
| EP | 069683 A1 | 1/1983 | | |
| EP | 0336774 A1 | 10/1989 | | |
| EP | 0346183 A1 | 12/1989 | | |
| EP | 0376658 A3 | 7/1990 | | |
| EP | 0502737 B1 | 9/1992 | | |
| EP | 0519873 B1 | 12/1992 | | |
| EP | 0 647 432 A1 | 10/1993 | | |
| EP | 0567705 B1 | 11/1993 | | |
| EP | 0600806 B1 | 6/1994 | | |
| EP | 0 685 210 A1 | 5/1995 | | |
| EP | 0674887 B1 | 10/1995 | | |
| EP | 0522822 B1 | 12/1995 | | |
| EP | 0 709 061 A1 | 5/1996 | | |
| EP | 0714645 B1 | 6/1996 | | |
| EP | 0 720 834 A2 | 7/1996 | | |
| EP | 0 720 834 A3 | 7/1996 | | |
| EP | 0749734 B1 | 12/1996 | | |
| EP | 0731676 B1 | 5/1997 | | |
| EP | 0 780 090 A1 | 6/1997 | | |
| EP | 0780 092 A1 | 6/1997 | | |
| EP | 0 824 904 A2 | 7/1997 | | |
| EP | 0781117 B1 | 7/1997 | | |
| EP | 0781533 B1 | 7/1997 | | |
| EP | 0 842 639 A2 | 5/1998 | | |
| EP | 0 824 904 A3 | 11/1998 | | |
| EP | 0891756 A2 | 1/1999 | | |
| EP | 0916322 A2 | 5/1999 | | |
| EP | 0913135 A3 | 6/1999 | | |
| EP | 0941719 A2 | 9/1999 | | |
| EP | 0985386 A2 | 3/2000 | | |
| EP | 0986994 A2 | 3/2000 | | |
| EP | 1 086 668 A1 | 3/2001 | | |
| EP | 1 084 680 A3 | 5/2001 | | |
| EP | 1099430 B1 | 5/2001 | | |
| EP | 1 149 562 A2 | 10/2001 | | |
| EP | 0634155 B1 | 10/2001 | | |
| EP | 1245204 A3 | 10/2002 | | |
| EP | 1216669 A3 | 10/2003 | | |
| EP | 1348408 A2 | 10/2003 | | |
| EP | 1380273 A2 | 1/2004 | | |
| EP | 1099430 B1 | 2/2004 | | |
| FR | 2141126 | 5/1972 | | |
| FR | 2589720 | 11/1985 | | |
| FR | 2621243 | 4/1989 | | |
| FR | 2682287 | * 4/1993 | 623/20.14 | |
| FR | 2682287 | 4/1993 | | |
| FR | 2768329 | * 9/1997 | 623/20.14 | |
| FR | 2768329 A | 3/1999 | | |
| GB | 2215610 A | 9/1989 | | |
| GB | 2355935 A | 5/2001 | | |
| WO | WO 79/00739 | 10/1979 | | |
| WO | WO 87/02882 | 5/1987 | | |
| WO | WO 87/02882 A1 | 5/1987 | | |
| WO | WO 98/02116 A1 | 1/1998 | | |
| WO | WO 98/20818 A1 | 5/1998 | | |
| WO | WO 98/46171 | 10/1998 | | |
| WO | WO 99/13803 A2 | 3/1999 | | |
| WO | WO 99/32053 | 7/1999 | | |
| WO | WO 00/23010 | 4/2000 | | |
| WO | WO 00/23011 A1 | 4/2000 | | |
| WO | WO 00/44316 A | 8/2000 | | |
| WO | WO 01/06961 A1 | 2/2001 | | |
| WO | WO 01/34069 A1 | 5/2001 | | |
| WO | WO 01/66021 A1 | 9/2001 | | |
| WO | WO 01/66022 A1 | 9/2001 | | |
| WO | WO 01/70142 A1 | 9/2001 | | |
| WO | WO0217821 | * 3/2002 | 623/20.15 | |
| WO | WO 03/070127 A1 | 8/2003 | | |

OTHER PUBLICATIONS

"The Subvastus Approach for Total Knee Arthroplasty Resulted in Better Short-Term Outcomes Than Did the Parapatellar Approach." G.S. Roysam and M.J. Oakley. The Journal of Bone & Joint Surgery. vol. 84 A, No. 2. Feb. 2002.

"Minimal Incision Total Knee Arthroplasty," Alfred J. Tria, Jr., MD and Thomas M. Coon, MD. Clinical Orthopaedics and Related Research. No. 416, pp. 185-190. Lippincott Williams & Wilkins, Inc. 2003.

"Minimally-Invasive Surgery (MIS) Quadriceps-Sparing Total Knee Replacement: New Quad Sparing Technique May Provide Faster Recovery for Patients with Arthritis of the Knee." Ed. Seth S. Leopold, MD. http://www.orthop.washington.edu/faculty/Leopold/quadsparing/01. Jul. 2, 2004.

"Richards Modular Knee System," Orthopedic Catalog, Richards, pp. 34-39 and 49 1979.

"Richards Mod II Knee," Marketing Materials, Link et al., 1976.

"The femorapatellar endoprosthesis—still of value today?", Fink et al., Z Ortrhop Ihre Grenzgeb., pp. 137(3):247-52, May-Jun. 1999.

"Bicondylar St. Georg Sledge Knee Arthroplasty," Stockley et al., Clinical Orthopaedics and Related Research, No. 255, pp. 228-233, Jun. 1990.

"New Jersey Low Contact Stress Knee Replacement System," Buechel and Pappas, Surgical Reconstruction and the Arthritic Knee II, p. 153, 1989.

"Patellofemoral Arthroplasty: A Three-to-Nine-Year Follow-up Study," Arciero et al., Clinical Orthopaedics and Related Research, No. 236, pp. 60-71, Nov. 1988.

"Kinematic I and Oxford Knee Arthroplasty—A 5-8-year Follow-Up Study," Bourne et al., 2 The Journal of Arthroplasty, No. 4, pp. 285-291, Dec. 1987.

"Failed Polycentric Total Knee Prostheses," Shoji et al., The Journal of Bone and Joint Surgery, vol. 58-4, No. 6, pp. 773-777, Sep. 1976.

European Search Report from PCT/US03/04750, which corresponds to U.S. Appl. No. 10/370,154.

* cited by examiner

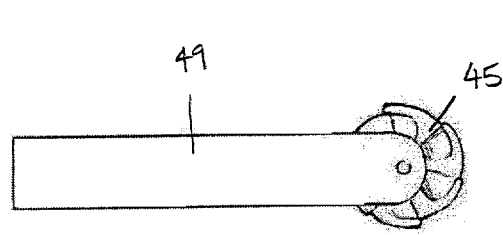
Figure 6
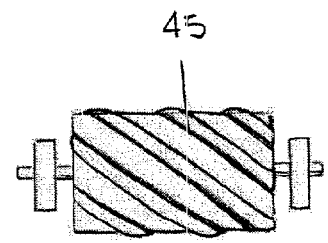
Figure 7
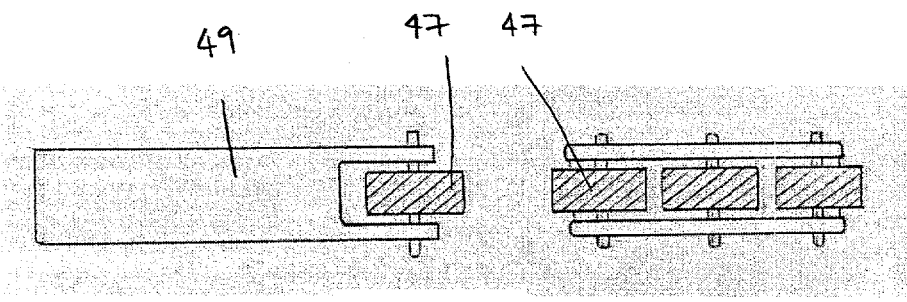
Figure 8
Figure 9
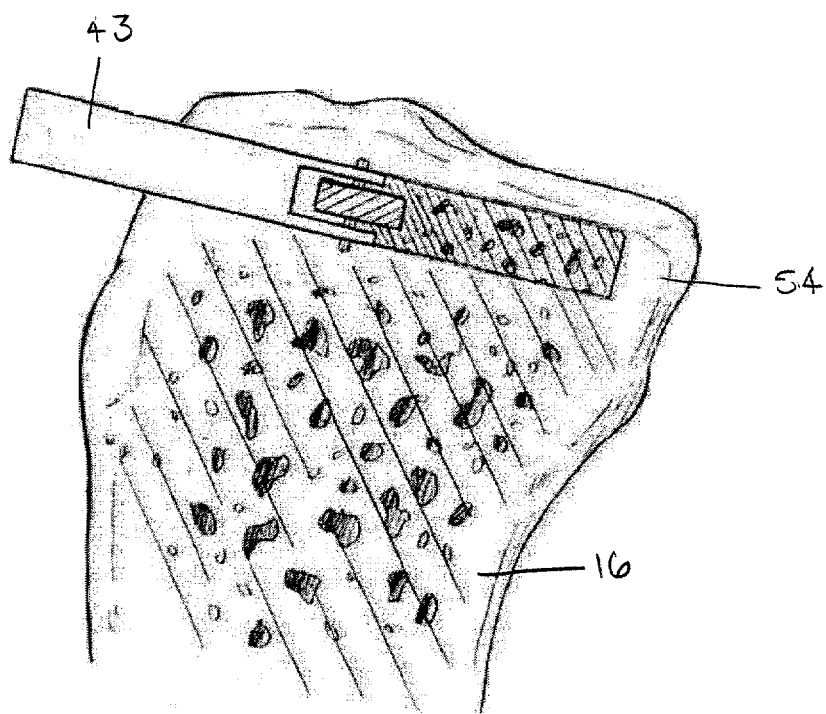
Figure 5

APPARATUS AND METHOD FOR SCULPTING THE SURFACE OF A JOINT

This application is a divisional application of commonly assigned patent application entitled Apparatus and Method for Sculpting the Surface of a Joint, Ser. No. 09/882,591, filed on Jun. 14, 2001 now U.S. Pat. No. 6,482,209.

BACKGROUND OF THE INVENTION

A joint generally consists of two relatively rigid bony structures that maintain a relationship with each other. Soft tissue structures spanning the bony structures hold the bony structures together and aid in defining the motion of one bony structure to the other. In the knee, for example, the bony structures are the tibia and the femur. Soft tissue such as ligaments, tendons, menisci, and capsule provide support to the tibia and femur. A smooth and resilient surface consisting of articular cartilage covers the bony structures. The articular surfaces of the bony structures work in concert with the soft tissue structures to form a mechanism that defines the envelop of motion between the structures. Within a typical envelop of motion, the bony structures move in a predetermined pattern with respect to one another. When fully articulated, the motion defines a total envelop of motion between the bony structures. The soft tissue structures spanning the knee joint tend to stabilize the knee in a transverse plane. This transverse stability enables the bony structures to slide and rotate on one another in an orderly fashion.

The articular surfaces are subject to a variety of diseases, accidents and the like that cause the surfaces to be damaged. A common disorder of joints is degenerative arthritis. Degenerative arthritis causes progressive pain, swelling, and stiffness of the joints. As the arthritic process develops, the joint surfaces wear away, resulting in contractures of the surrounding soft tissues that provide stability to the joint. Changes in the articular surfaces resulting from arthritis decrease stability and increase the translation of the joint.

Treatment of the afflicted articular bone surfaces depends, among other things, upon the severity of the damage to the articular surface and the age and general physical robustness of the patient. The end result commonly necessitates joint replacement surgery wherein the articulating elements of the joint are replaced with artificial elements commonly consisting of a part made of metal articulating with a part made of ultra high molecular weight polyethylene (UHMWPE).

A relatively young patient with moderate to severe degeneration of the knee joint is often treated with drug therapies. While drug therapies may temporarily provide relief of pain, progression of the disease, with resulting deformity and reduced function, ultimately necessitates surgery. Alternative treatments such as nonsteroidal anti-inflammatory drugs, cortisone injections, and arthroscopic debridement similarly provide only temporary relief of symptoms.

In severe situations, the entire articular surface of a bone may be replaced with an artificial surface, as, for example, when condyles at the distal end of the femur are largely replaced with a prosthetic device having polished metal condyles and the tibial plateau is replaced with a plastic bearing that may be supported by a metal component. Joint replacement surgery has become a proven and efficacious method of alleviating pain and restoring function of the joint.

Current methods of preparing the intraarticular rigid elements of a joint to receive components as in joint replacement surgery involve an extensive surgical exposure. The exposure must be sufficient to permit the introduction of guides that are placed on, in, or attach to the joint, along with cutting blocks to guide the use of saws, burrs and other milling devices, and other instruments for cutting or removing cartilage and bone that subsequently is replaced with artificial surfaces. The distal end of the femur may be sculpted to have flat anterior and posterior surfaces generally parallel to the length of the femur, a flat end surface normal to the anterior and posterior surfaces, and angled flat surfaces joining the above mentioned surfaces, all for the purpose of receiving a prosthetic device.

A full joint replacement, using the example of the knee joint, also requires the proximal end of the tibia to be sculpted to receive a prosthesis having a generally upwardly facing bearing surface mimicking the normal tibial bearing surface and designed to articulate with the condylar surfaces of the femoral prosthesis. Typically, this surgery is performed with instruments or guides to orient cutting blocks, such that the preparation of the bone is in concordance with the correct alignment of the limb and the parts are correctly oriented in both coronal and sagittal positions. The guides are placed on exposed bones and generally reference anatomical points on that bone to establish a resection plane. For instance, with total knee replacement, arthroplasty guides are used by referencing, for example, the intramedullary cavity and the epicondylar and posterior condylar axes.

Knee joint prosthesis of the type referred to above are well known, and are described, for example, in Caspari et. al., U.S. Pat. Nos. 5,171,244, 5,171,276 and 5,336,266, Brown, U.S. Pat. No. 4,892,547, Burstein et al., U.S. Pat. No. 4,298,992, and Insall et. al., U.S. Pat. No. 6,068,658.

Substantial effort has been made to provide appropriate degrees of curvature to the condyles. For example, the earlier mentioned U.S. Pat. Nos. 5,171,276, 4,298,992 and 6,068,658 show that the radius of curvature in the anterior-posterior direction of the condyle of a femoral prosthesis may be somewhat greater near the anterior portion of the condyle than near the posterior portion. Kester et al., U.S. Pat. No. 5,824,100 teaches that a portion of this curvature of the condyle may be formed about a constant radius having its origin along a line between the lateral and medial collateral ligament attachment points on the femur.

Historically, a variety of modular prosthetic joint implants have been developed. The following descriptions of modular implants relate specifically to the knee. Early designs for knee implants, called polycentric knee implants, were developed with separate components for the medial and lateral compartments. Additionally, modular fixed-bearing knee implants having a polyethylene insert that is held relatively rigidly in place have been developed. Alternately, there are mobile bearing knee implants wherein the polyethylene bearing is designed to slide or move with minimal or no constraint on a tibial baseplate. Furthermore, both meniscal bearing and fixed bearing knee implants have been developed including either separate polyethylene bearings or a single polyethylene bearing that resides on a metallic tibial baseplate. While implant systems have been developed with fixed bearing elements or mobile bearing elements on the medial and lateral sides of the tibiofemoral joint, systems have not been developed having a combination of a fixed bearing on one side and a mobile bearing on the other side of the tibiofemoral joint.

Mobile bearing tibial implants may be configured to be more congruent with the femoral side of a knee arthroplasty, yielding lower contact stress. The resultant lower contact stress reduces the possibility of damage sometimes encountered with some fixed bearing designs wherein the yield strength of the bearing material is exceeded. In general, fixed bearing implant designs are less difficult to properly align and balance than mobile bearing designs. Mobile bearing designs are frequently desirable to reduce contact stress and the resulting wear of the bearing surface. However, with mobile bearing designs, there is the possibility of the bearing becoming dislodged from the implant. Additionally, mobile bearing knee designs are more surgically demanding to implant then fixed bearing designs.

The combination of a fixed bearing insert for the medial compartment and a mobile bearing insert for the lateral compartment is particularly attractive because the lateral femoral condyle rolls backward on the lateral tibial plateau as much as 10 to 20 mm whereas the medial condyle moves only a few millimeters. A mobile bearing insert is able to accommodate the rollback of the lateral condyle but would not be necessary for the medial condyle.

Two primary difficulties exist with current joint replacement surgeries. These relate to the invasiveness of the procedure and achieving proper alignment of the bony structures and the prostheses thereupon.

Alignment. A difficulty with implanting both modular and non-modular knee implants having either separate femoral and/or tibial components has been achieving a correct relationship between the components. Surgical instruments available to date have not provided trouble free use in implanting multi-part implants wherein the femur and tibia are prepared for precise component-to-component orientation. While alignment guides aid in accurate orientation of the components relative to the axis of the long bones to achieve a restoration of a correct tibiofemoral alignment (usually 4–7 degrees valgus), they provide limited positioning or guidance relevant to correct component-to-component alignment and/or ligament tension to restore alignment.

It is preferable to orient implants normal to the resultant forces through the joint to subject bearing surfaces to compressive rather than shear forces. Moreover, the components of the implant are preferably oriented one to the other to minimize wear. Complications may result if the implant is not correctly oriented with respect to the supporting bone. If the implant is not placed normal to the mechanical axis, a shearing force results between the implant and bone that may lead to implant loosening.

In a properly aligned knee, the mechanical axis of the leg (a straight line drawn from the center of the hip joint to the center of the ankle) passes slightly medial to the center of the knee. This alignment is generally called the gross alignment of the leg. The alignment of the implants impacts the gross alignment of the leg. If the implants are malaligned, the resulting mechanical axis may be shifted medially or laterally, resulting in an imbalance in the loads carried by the medial or lateral condyles. This imbalance, if severe, may lead to early failure of the implant.

In addition, the orientation of the components to each other, for example the orientation of the femoral to the tibial component, with unicondylar and bicondylar implants has largely not been addressed. This may account for the high failure rates of early bicondylar designs and as well as for the higher failure rate of unicondylar implants relative to total knee implants as demonstrated in some clinical studies. When considering bicondylar and unicondylar designs, alignment of each part relative to the other parts is critical to avoid accelerated wear with a mal-articulation of the components.

Although various prosthetic devices have been successfully used with patients, the configuration and position of the articulating surfaces of the prosthesis, that is, for example, the condyles in a knee joint are predetermined based upon the prosthesis that is selected. While efforts are made to tailor the prosthesis to the needs of each patient by suitable prosthesis choice and size, this in fact is problematical inasmuch as the joint physiology of patients can vary substantially from one patient to another.

Invasiveness. In order to appropriately sculpt the articulating surface of a bone, it is often necessary to surgically expose the joint. In the case of the femur, the patellar tendon of the knee joint is surgically exposed and is moved to one side of the joint to enable a substantially full anterior access to the joint. Surgical exposure is necessary to accommodate the bulk and geometry of the components as well as the instruments for bone preparation. Such surgical exposure increases bleeding, pain, and muscle inhibition; all of which contribute to a longer hospitalization before the patient can be safely discharged to home or an intermediate care facility.

Desirably, in the case of knee replacement surgery, neither the collateral ligaments nor the cruciate ligaments are disturbed, although it is often necessary to remove or release cruciate ligaments in the event a substantial joint replacement is to be performed. Collateral ligaments can be partially taken down or released to provide appropriate tension adjustment to the patient's knee in concert with joint replacement surgery. In most instances, such releases can be accomplished through smaller incisions than the standard midline or medial parapatellar incisions historically used for knee arthroplasty.

Arthroscopic surgery is available, and beneficial, for removing and repairing damaged intraarticular tissues. Although arthroscopic procedures are far less invasive and are often successful for minor surgical repairs, (as when an articular surface is to be smoothed, for example, or cartilage is to be repaired), such procedures generally are not appropriate for substantial joint replacement. They are generally inadequate for replacing joint surfaces with artificial implants.

Conventional surgical procedures including unicompartmental and total joint replacement historically require extensive surgical exposure and prolonged hospital stays and rehabilitation. More recently unicondylar procedures have been performed through smaller incisions that do not necessitate dislocation of the patella. The reduction in pain and more rapid recovery of knee function has reduced the length of hospital stay and the need for strong narcotic medications. It is desirable to realize such benefits for patients with bicompartmental and tricompartmental knee arthroplasty.

For patients who require articular surface replacement, including patients whose joints are not so damaged or diseased as to require whole joint replacement, it would be desirable to provide surgical methods and apparatuses that could be employed to gain surgical access to articulating joint surfaces, to appropriately sculpt the surfaces, to provide artificial, e.g., metal or plastic, articular bearing surfaces, and then to close the surgical site, all without substantial damage or trauma to associated ligaments and tendons. To reach this goal, of course, a procedure must be provided to enable articulating surfaces of the joints to be appropriately sculpted using minimally invasive apparatuses and procedures.

SUMMARY OF THE INVENTION

The present invention provides an implant system that restores individual patient joint kinematics and involves minimally invasive surgical procedures. The instruments and implants disclosed accomplish accurate bone and soft tissue preparation, implant orientation and implant fixation through limited surgical exposure. The implant system is comprised of implants and instrumentation that provide intraoperative surgical options for articular constraint and facilitate proper alignment and orientation of the knee to restore kinematics as defined by the individual patient anatomy. To do so, the implants provide a surgeon intraoperative options to reconstruct various degrees of joint stability via selection of fixed or mobile bearing components for each compartment of the knee (medial tibiofemoral joint, lateral tibiofemoral joint and patellofemoral joint). The range of implants may cover each compartment of the knee and may include combinations of fixed and mobile bearing configurations.

In traditional total knee replacements, the femoral component is generally a unitary piece and the tibial component is a unitary piece. In the current invention, the femoral side may be resurfaced by two or three components and the tibial side may be resurfaced by two components or a unitary piece. Optionally, the components of the femoral side may be comprised of a plurality of flexible segments.

Proper alignment and positioning of the implant components is facilitated by instrumentation that utilizes the soft tissue structures of the knee to guide bony resections for patient-specific alignment and orientation of the implants. The surgical instrumentation prepares the articular surfaces of a synovial joint from a single point of reference to allow the introduction of separate components for the medial and lateral tibiofemoral compartments, and the patellofemoral compartments with precise orientation. Thus, the instrumentation provides bony resections in accordance with such alignment and orientation requirements. The alignment positioning is important for proper restoration of anatomic alignment of the knee joint and for proper orientation of the components to one another.

With respect to forming or sculpting articular surfaces of a joint, the method of the current invention enables the articular bone surfaces to be sculpted according to the individual physiology of each patient to restore as much as possible the natural junction of the joint. In this method, a bone sculpting tool is attached to one of the bones of a joint, and the tool sculpts the articular surface of the other bone as the joint is articulated.

Thus, in one embodiment, the present invention provides a method of appropriately sculpting the articular surface of a first bone that normally articulates with a second bone. The method involves providing an apparatus comprising a bone sculpting tool attached to a bone mount, attaching the mount rigidly to the second bone with the tool in bone sculpting engagement with the articular surface of the first bone, and then sculpting the articular surface by articulating one of the bones with respect to the other.

In some situations, it may be desirable to distract the first bone from the second bone either preoperatively or during surgery. Thus, a distractor may be provided with the apparatus. A distraction force provided between the femur and the tibia during the sculpting procedure accounts for material that has worn away from the articular surfaces. Use of a distraction force generally re-establishes normal alignment of the joint. Additionally, a distractor may be used preoperatively to assess the range of motion of the joint and patient kinematics.

In another embodiment, the invention provides an apparatus for sculpting the articular surface of a first bone that normally articulates in a predetermined manner with the second bone. The apparatus comprises a bone sculpting tool, a mount attachable rigidly to the second bone, and an adjustable attachment attaching the sculpting tool to the mount and enabling the position and orientation of the tool to be adjusted into bone-sculpting proximity to the articular surface so that the articular surface is sculpted as the second bone is articulated with respect to the first bone. Alternately, a plurality of bone sculpting tools may be used where the tools are positioned either on individual mounts or on a single mount to support the plurality of tools.

The invention also provides implants for replacing the surfaces of the joint between the first bone and the second bone. The implants are specifically designed to fit through minimally invasive incisions and incorporates any and all combinations of fixed and mobile bearing inserts or parts. Since the surgical procedure preferably is performed through minimally invasive incisions the implants are designed to fit through such incisions and be either oriented or joined within the joint.

The implants include a second bone baseplate and a first bone implant. The second bone baseplate may be either one piece to cover most of the prepared surface of the second bone as relates to the joint, or separate baseplates as have been used with mobile and fixed bearing prosthetic components. In addition, the second bone baseplate may accommodate separate fixed and mobile bearing inserts. The first bone implant is comprised of a plurality of components to replace the bearing surface of the first bone. Optionally, a portion of the first bone implant may be configured of a plurality of flexible segments bonded in place. Such a configuration permits the articulation of the second bone to the first bone to mould the flexible segments in appropriate position.

Thus, in a further embodiment, the invention provides a method of appropriately replacing the articular surface of a first bone that normally articulates with a second bone. The method involves providing an apparatus comprising a bone sculpting tool attached to a bone mount, attaching the mount rigidly to the second bone with the tool in bone sculpting engagement with the articular surface of the first bone, and then sculpting the articular surface by articulating one of the bones with respect to the other. Further, resurfacing the articular surfaces with appropriate minimally invasive implants wherein the implants are joined within the confines of the joint cavity. In one embodiment, a plurality of flexible segments are provided to resurface a portion of the first bone. The flexible segments are set in an adhesive along the resected surface of the first bone.

Specifically, for example, the invention may be used for replacing the surfaces of a femur and a tibia. Thus, a femoral implant having a plurality of components and a tibial baseplate are provided. The tibial baseplate may have a fixed bearing attachment as well as a mobile bearing attachment.

BRIEF DESCRIPTION OF THE DRAWING

FIG. 5 illustrates a cross-sectional view of the a cavity created in the tibial plateau in accordance with one embodiment of the present invention.

FIG. 6 shows a plan view of an instrument for creating a resection in the tibial plateau according to one embodiment of the present invention.

FIG. 7 shows an end view of the instrument of FIG. 6.

FIG. 8 shows a plan view of an instrument for creating a resection in the tibial plateau according to a second embodiment of the present invention.

FIG. 9 shows an end view of the instrument of FIG. 8.

DETAILED DESCRIPTION OF THE PREFERRED EMBODIMENT

Figure 1:
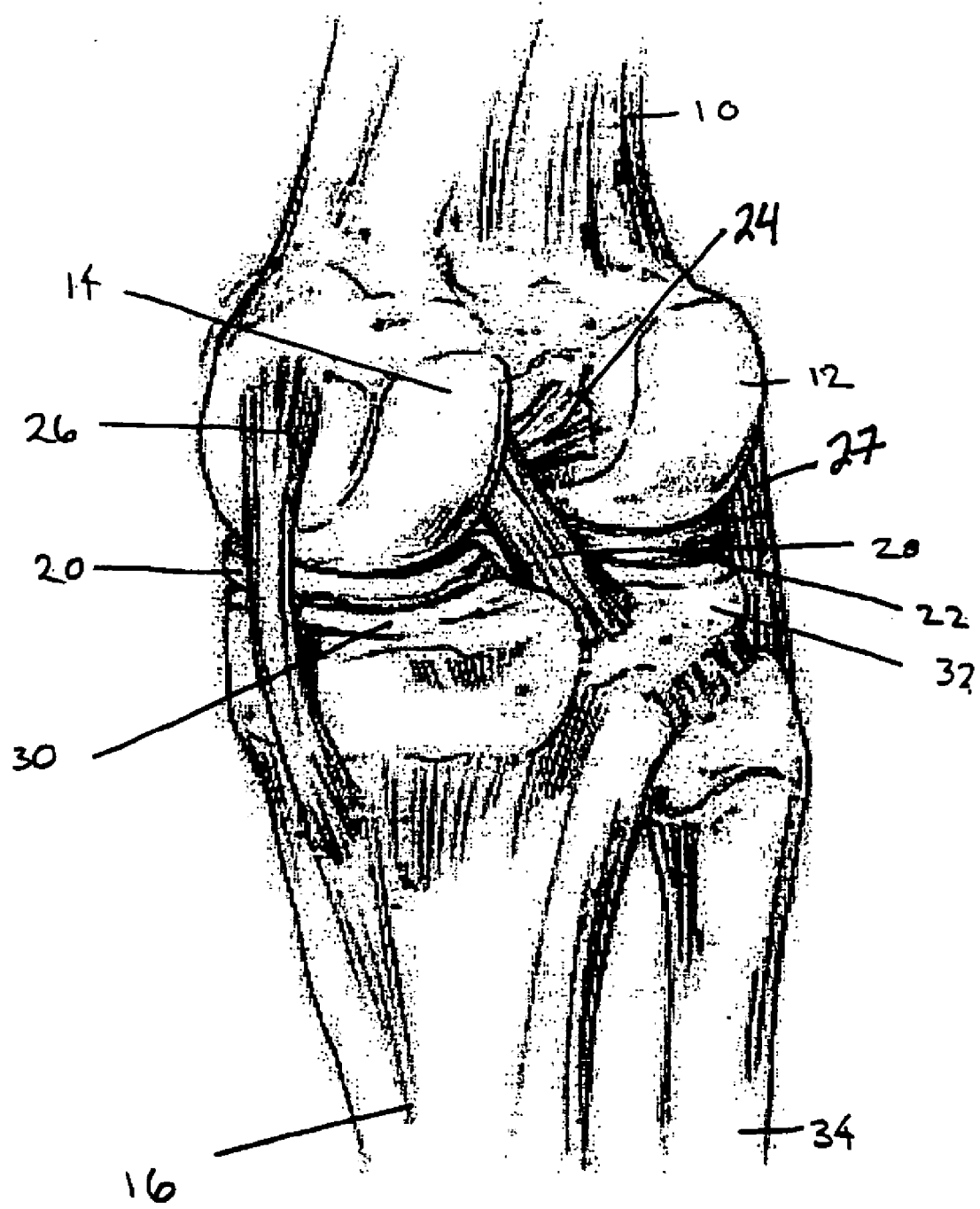
FIG. 1 shows a plan view of knee joint.

FIG. 1 illustrates the general anatomy of the knee joint. The femur 10 has the lateral femoral condyle 12 and the medial femoral condyle 14 on its knee-joint articulating surface. The tibia 16 has the lateral meniscus 22 (generally opposite the lateral femoral condyle 12) and the medial meniscus 20 (generally opposite the medial femoral condyle 14) on its knee-joint articulating surface. The anterior cruciate ligament 24, the posterior cruciate ligament 28, the medial collateral ligament 26 and the lateral collateral ligament 27. The medial tibial condyle 30 and the lateral tibial condyle 32 support the menisci 20 and 22, which in turn support the femur 10. Additionally, the fibula 34 engages the tibia 16.

Typically, a total knee joint replacement involves replacing the articular surfaces of the lateral femoral condyle 12, the medial femoral condyle 14, the medial tibial condyle 30 and the lateral tibial condyle 32. The lateral meniscus 22, and the medical meniscus 20 are removed. Desirably, neither the collateral ligaments 26 and 27 nor the cruciate ligaments 24 and 28 are disturbed. However, the collateral ligaments 26 and 27 may be partially taken down to provide appropriate tension adjustments to the patient's knee after joint replacement has been completed.

Figure 2:
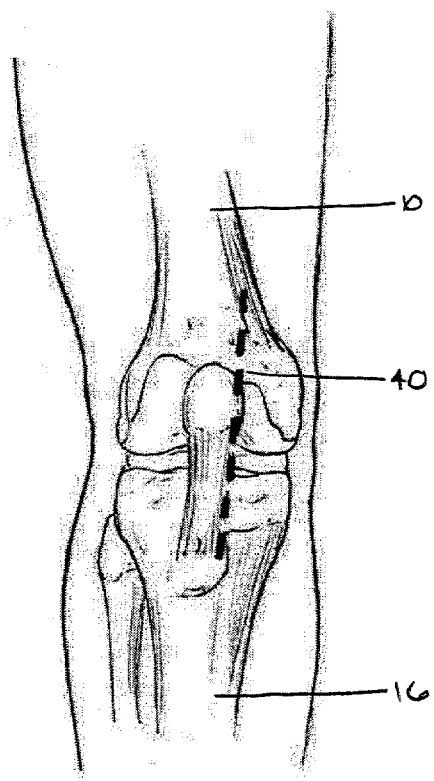
FIG. 2 shows a traditional midline incision for accessing the knee joint during total knee replacement surgery.

FIG. 2 illustrates the conventional midline incision 40 for a total knee replacement surgery. The incision 40 extends vertically substantially above and below the articulating surface between femur and the tibia. Typically, the incision is roughly 8 to 15 centimeters in length. The incision 40 must be large enough to expose the entire knee joint articular surfaces with the patella subluxed or dislocated. Additionally, the incision must accommodate insertion of components that fully cover the end of the femur, the top of the tibia and the undersurface of the patella. The maximum number of components implanted would include femoral and tibial components for the lateral tibiofemoral compartment, femoral and tibial components for the medial tibiofemoral compartment and femoral and patellar components for the patellofemoral joint. Alternatively, the lateral femoral condyle and the patellar groove may be covered by a common implant.

Figure 3:
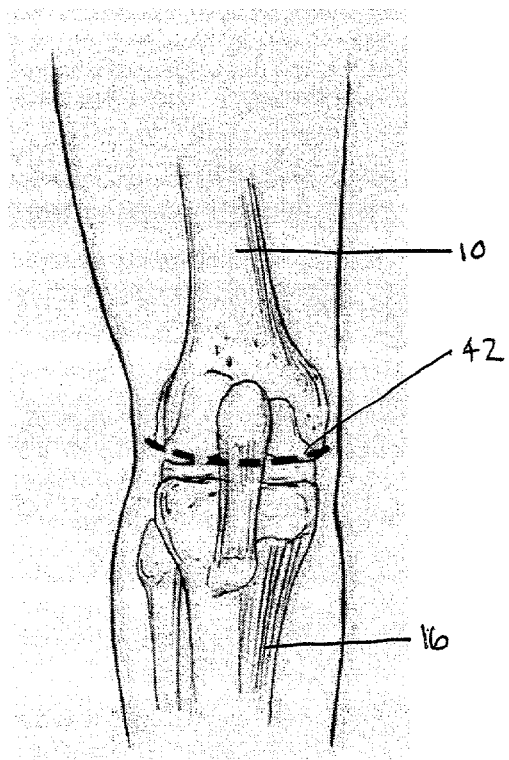
FIG. 3 shows an incision for accessing the knee joint during total knee replacement surgery that may be used in with the method and apparatus of the present invention.

As seen in FIG. 3, transverse incision 42 extending horizontally along the knee joint is one option for the procedure of the present invention. Incision 42 may be vertically opened to expose the joint surfaces of the medial tibiofemoral compartment and the lateral tibiofemoral compartment without dislocating the patella. This keeps the patella in contact with the femur during the procedure. The components of the instrumentation as well as the implant are sized for minimal invasiveness and, therefore, may be accommodated by the small incision. The reduced trauma resulting from a smaller incision generally results in faster and better rehabilitation, which in turn generally increases the efficacy of the knee implant.

Figure 4:
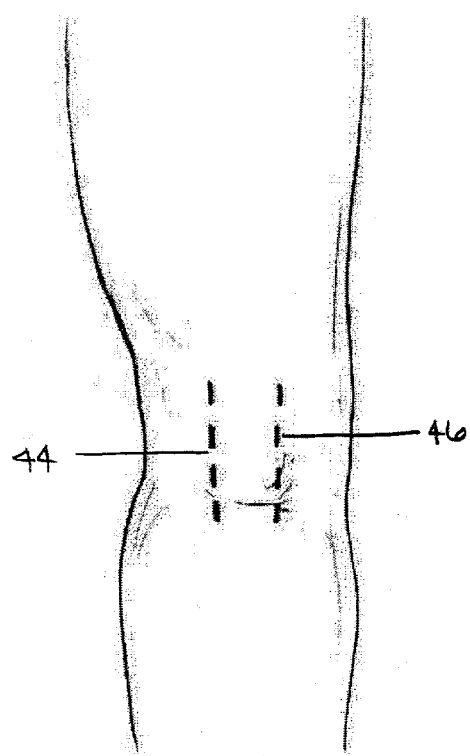
FIG. 4 shows alternate incisions for accessing the knee joint during total knee replacement surgery that may be used in with the method and apparatus of the present invention.

FIG. 4 depicts an alternate incision format for use with the present invention. Two parallel vertically extending incisions 44 and 46 may be formed on either side of the patella. These incisions 44 and 46 are relatively short and the invasiveness is similar to that of the horizontal incision in FIG. 3. Each incision 44 and 46 is separately extended through the joint capsule to expose the medial and lateral tibiofemoral compartments without dislocating the patella.

Instrumentation.

The instrumentation of the current invention generally calls for resecting the tibia at the lateral tibial plateau and the medial tibial plateau. This resection may be done by methods known by those skilled in the art, using a resection guide, saw, etc. Alternately, as shown in FIG. 5, a milling burr 43 may be advanced directly into the tibia 16. Milling burr 43 should stop at or short of the posterior cortical wall 54. FIG. 5 shows a cross sectional view through the cavity created in the tibial plateau by the milling burrs 47 of FIGS. 6 and 7.

As seen in FIGS. 6 and 7, the cutting device may be a single milling burr 45 affixed at the forward end of guide element 49. The milling burr 45 of FIGS. 6 and 7 has its axel in a medial to lateral direction when preparing the tibial plateau. The radius of the milling burr leaves a corresponding radius between the floor and posterior wall of the cavity created.

Alternately, as seen in FIGS. 8 and 9, the cutting device may be a plurality of milling burrs 47. The milling burrs 47 of FIGS. 8 and 9 prepare a corner between the floor and posterior wall of the cavity created in the tibial plateau. The corner thus prepared may distribute stress uniformly into the supporting bone. The milling burrs 47 create a radius equivalent to the radius of the burr between the sidewalls of the cavity and the posterior wall. Such a radius is easily accommodated by the tibial implant design. While FIGS. 8 and 9 depict a cutting device having a plurality of milling burrs, the cutting device may be configured with one milling burr.

Figure 10:
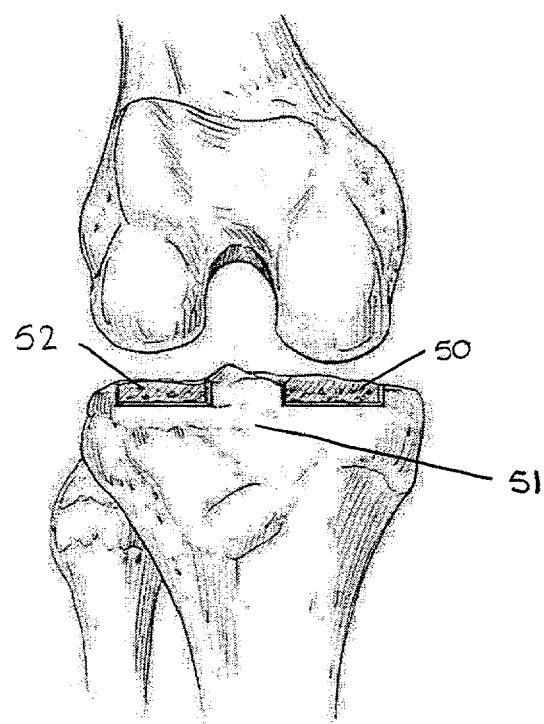
FIG. 10 shows a plan view of tibial resections formed in accordance with the present invention.

FIG. 10 shows an anterior view of the bone resections 50 and 52 that are made in the tibial plateau, generally 51. The floor of the medial resection 50 and the floor of the lateral resection 52 are preferably parallel and co-planar to ensure proper alignment and orientation of the medial and lateral tibial components. The external tools used to guide the tibial cutter may provide relative alignment between the medial and lateral resections. Alternately, the medial and lateral cavities in the tibial plateau may be prepared simultaneously by having two guide elements 49 linked together by a hinge that restrains the medial and lateral milling burrs 47 in a common plane. The external tools may further provide a positive reference to the posterior aspect of the tibial plateau to ensure that the resections do not penetrate the posterior cortical wall. In FIG. 10, the bone resections are shown to have a generally rectangular cross-section. However, any cross-section to which a bone sculpting tool may be mounted may be used. For example, an arcuate cross-section is acceptable.

Figure 11:
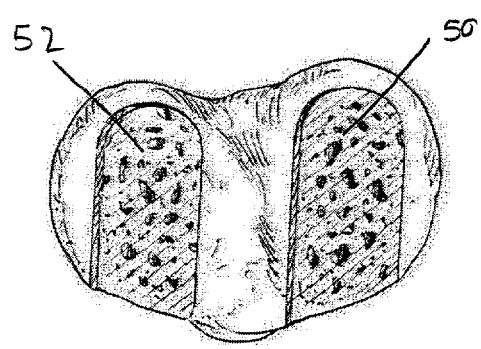
FIG. 11 shows a top view of the resections shown in FIG. 10.
Figure 12:
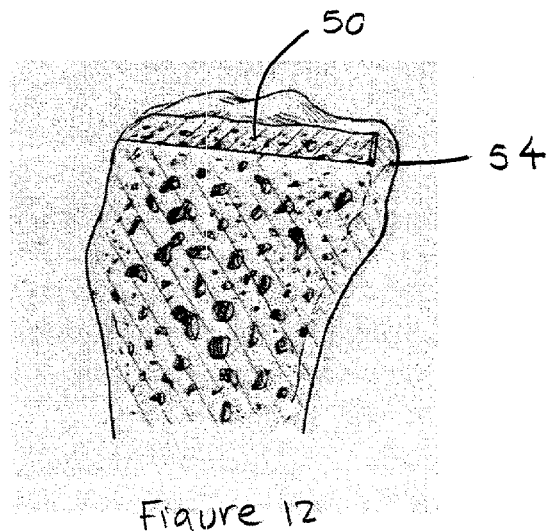
FIG. 12 shows a cross-sectional view of one of the resections shown in FIG. 10.

FIG. 11 shows a top-view of bone resections 50 and 52 in the tibia 16. A cross-sectional view of tibia 16 with a cavity machined into the plateau is depicted in FIG. 12. As seen in FIG. 12, the bone resection 50 should stop at or short of the posterior cortical wall 54.

Figure 13:
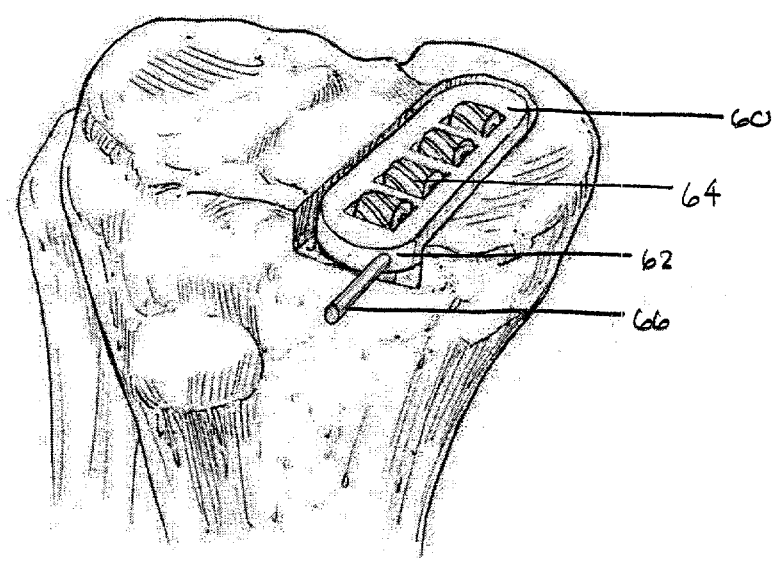
FIG. 13 shows a plan view of one embodiment of the present invention having a cutting attached to a tibial resection.
Figure 14:
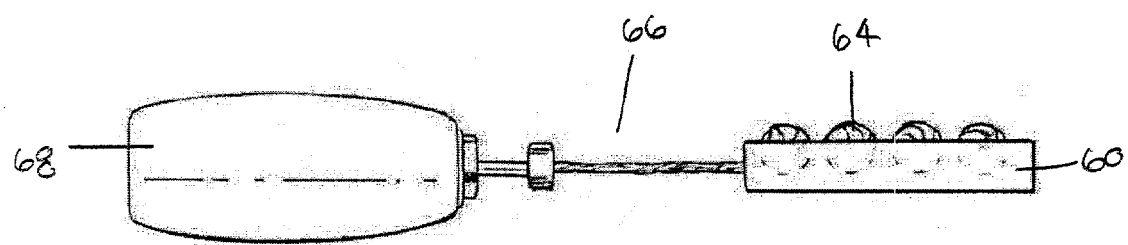
FIG. 14 shows a side view of a configuration of the cutting element of FIG. 13 connected to a motor according to an alternate embodiment of the present invention.

As seen in FIG. 13, upon resection of the tibia, a bone sculpting tool, for example, a femoral cutter, generally 60, is placed in a mount and rigidly attached to the cavity created in the tibia. Rigid attachment generally means providing sufficient stability to prevent relative motion between the mount and the tibia during articulation. Such stability may be provided through mere placement of the device in the tibial resection. The femoral cutter is designed to reference the tibial resections 50 and 52 when making the femoral resections. In one embodiment, illustrated in FIG. 13, the mount is a cradle 62 and is set in the resected tibia. Cutting elements 64 are mounted in the cradle 62 and a flexible shaft 66 connects the cutting element to a motor 68 of FIG. 14. The device fits into the resections 50 and 52 in the tibial medial and lateral plateaus. Thus, a cutting element is rigidly held against the femoral condyle and the guide surface of the device sets the depth of resection. Optionally, a second cutting element may be placed in the opposite tibial resection. Thus, for example, two cutting elements may be placed in the prepared tibial plateau, one in the medial cavity and one in the lateral cavity, and may be used to simultaneously resect the femoral condyles. In using two cutting elements simultaneously, the cutting elements may be linked together by a hinge mechanism 62 to further maintain the cutting elements in a common plane while preparing the femoral condyles (Reference is made to FIGS. 32 and 33).

Thus, for example, in knee surgery, the tool may be mounted to the tibia with the sculpting surface of the tool in engagement with a condylar surface of the femur that is, one or both of the condyles. As the knee joint is articulated (flexed), the sculpting tool appropriately sculpts the articular surface of the femur in a manner that is dependent upon the individual physiology of that patient's knee, that is, upon the collateral ligaments, the patellar tendon, etc. Although the invention is described in the context of a total knee replacement, it is understood that the invention has application throughout orthopaedics where the surfaces of an articulating joint are to be modified or resurfaced to restore function and relieve pain.

In a preferred embodiment, the knee joint capsule is surgically accessed without lateral dislocation of the patella, thereby permitting normal flexion of the knee during the sculpting process. The patient's individual physiology and the interplay between the patient's soft tissues and bone work to guide the device used for sculpting cartilage and bone from the end of the femur and/or tibia as relates to the knee. In the example of the knee, the tibia travels around the end of the femur along a guided path that is controlled by the ligaments and soft tissues that surround and provide support to the knee.

An alternate mount configuration involves an external fixture having burrs attached thereto. The external fixture may be of any configuration that supports the burrs in a position relative to the tibia for sculpting the femur. One example includes an external support member having an arm extending therefrom, the burr attached at the distal end of the arm.

The motor may be an electric motor, a pneumatic motor, or a hydraulic motor integral with the cutting element. Note that in the case of a hydraulic motor, the flexible shaft is not necessary. The cutting element may be driven by available surgical power instruments, such as surgical drills, Midas Rex and Anspaq hi speed drill/cutters, etc. Such equipment is available in pneumatic and battery operated forms. The cutting element may alternately be driven by a power source developed uniquely for this invention. For example, the power source may be an electric or pneumatic motor. It may also be a hydraulic motor driven by sterile saline solution.

Figure 15:
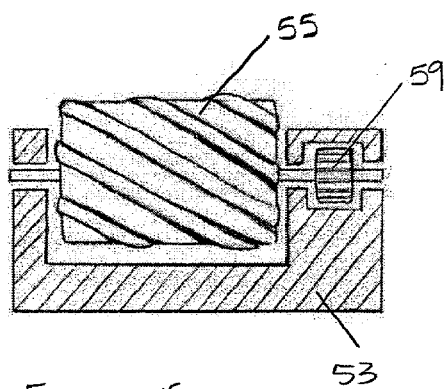
FIGS. 15 and 16 show alternate views of a cutting element driven by a hydraulic motor in accordance to one embodiment of the present invention.
Figure 16:
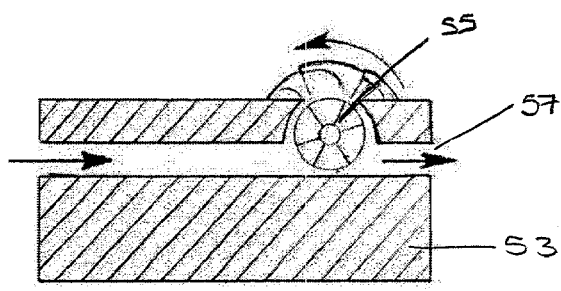
Figure 17:
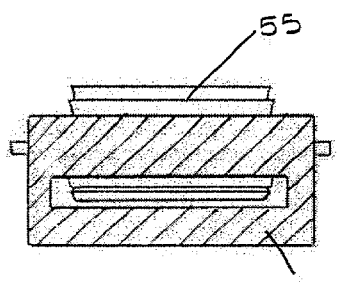
FIGS. 17 and 18 show alternate views of a cutting element driven by a hydraulic motor in accordance to an alternate embodiment of the present invention.
Figure 18:
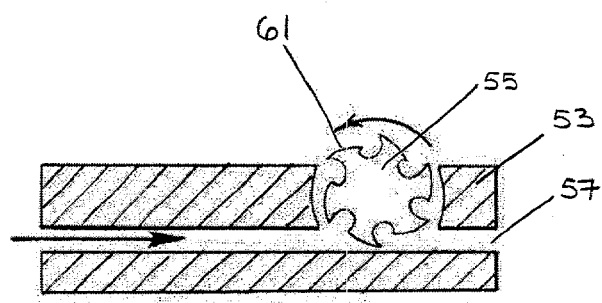

In the case of a hydraulic motor driven with saline solution, the motor may be incorporated into the milling cutter, as illustrated in FIGS. 15 through 18. The vanes of the hydraulic motor are optionally machined as part of the axial of the milling burr element, or machined into the end face of the milling burr element. Preferably, the housing 53 of the cutting device 55 includes a channel 57 for accommodating saline solution to drive the hydraulic motor. FIGS. 15 and 16 show an embodiment wherein the vanes of the hydraulic motor are incorporated into the wheel 59 at the distal end of the housing 53. It is also possible, as seen in FIGS. 17 and 18, to have the blades 61 of the cutting element 55 function as the vanes of the hydraulic motor in which case the saline solution is directed against the cutting element to force rotation.

Figure 19:
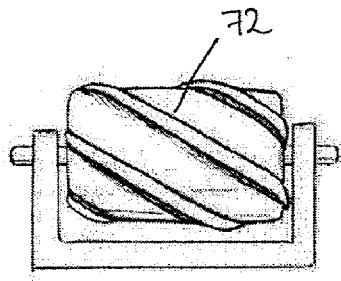
FIG. 19 shows an end view of a cutting element in accordance with one embodiment of the present invention.
Figure 20:
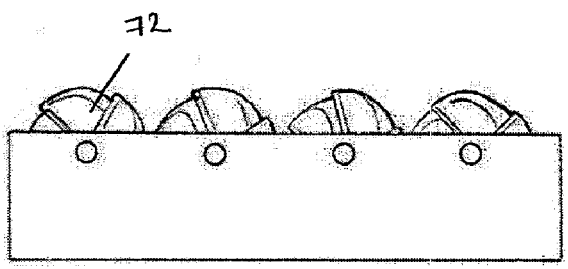
FIG. 20 shows a side view of the cutting element of FIG. 19.

FIGS. 19 through 30 depict cross-sectional views of various cutting elements that may be used with the present invention. FIGS. 19 and 20 show an end and side view, respectively, of one embodiment of a cutting element. Milling burrs 72 are placed in mount 73 and orientated with the axels in a medial to later direction. Multiple milling burrs are shown to provide contact with the femoral condyle as the knee is flexed and the tibiofemoral contact point moves distally. Alternately, one milling burr may be placed in a position that it remains in contact with the femoral condyle throughout knee flexion. Although only the options of one or four milling burrs are depicted, the invention may be practiced with one or more milling burrs supported in the cradle. Further, the cradle may be provided with shoulders 71 having skidding surfaces for contacting the femoral condyle.

Figure 21:
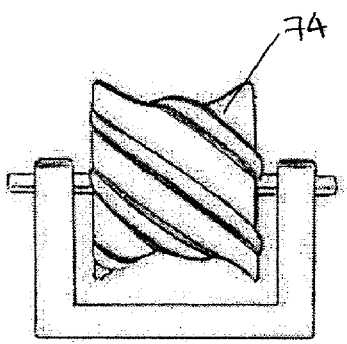
FIG. 21 shows an end view of a cutting element in accordance with a second embodiment of the present invention.
Figure 22:
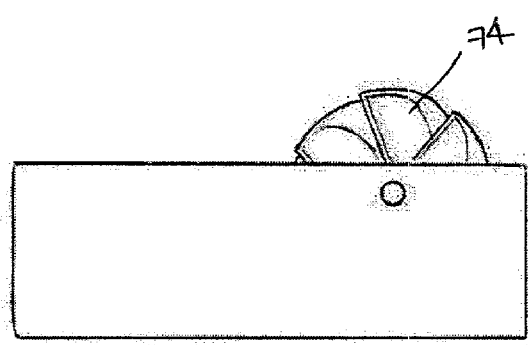
FIG. 22 shows a side view of the cutting element of FIG. 21.

FIGS. 21 and 22 shows an end view and a side view, respectively, of an alternate embodiment for a cutting element in which the milling burr 74 is contoured to provide a contoured resection in the femoral condyle. A contoured resection removes less bone and the bone remaining is generally stronger than bone deeper in the condyle.

Figure 23:
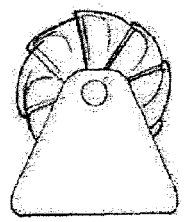
FIG. 23 shows an end view of a cutting element in accordance with a third embodiment of the present invention.
Figure 24:
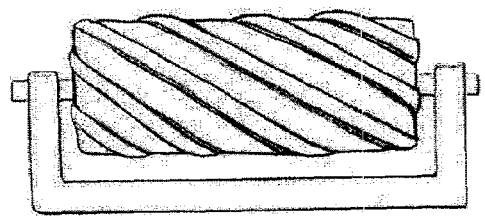
FIG. 24 shows a side view of the cutting element of FIG. 23.

In an other embodiment as shown in FIGS. 23 and 24, the milling burr 72 is oriented with its axel in an anterior to posterior direction. At knee extension, the tibiofemoral contact point is near the anterior end of the milling burr. As the knee is flexed, the contact point moves posterior and approaches the posterior end of the milling cutter.

Figure 27:
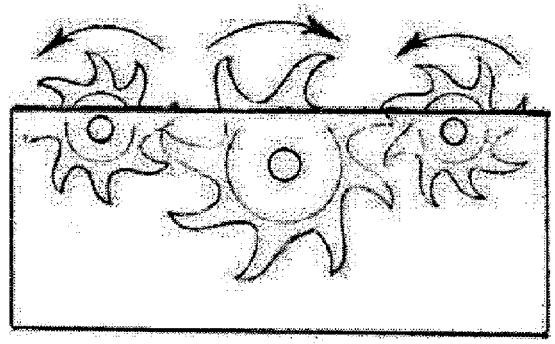
FIG. 27 shows a cross-sectional view of the cutting element of FIG. 25.
Figure 25:
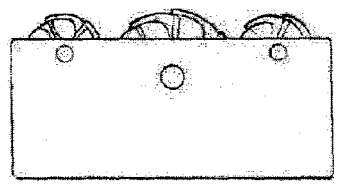
FIG. 25 shows a side view of a cutting element in accordance with a fourth embodiment of the present invention.
Figure 26:
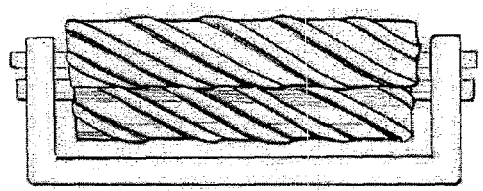
FIG. 26 shows an end view of the cutting element of FIG. 25.

In similar fashion, FIGS. 25 and 26 show three milling burrs 76, 77, and 78 in parallel with axels orientated in an anterior to posterior direction. Such an embodiment provides for a broad resection of the femoral condyle in one pass or flexion of the tibia. The medial and lateral milling burrs 76 and 78 may be of smaller diameter than the central milling burr 77, as seen in FIG. 27, to provide a smaller corresponding radius between the sidewalls of the cavity created in the femoral condyle and the floor of the cavity.

Figure 28:
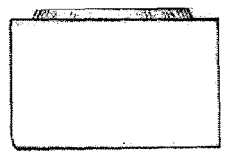
FIG. 28 shows an end view of a cutting element in accordance with a fifth embodiment of the present invention.
Figure 29:
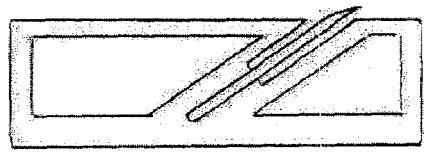
FIG. 29 show a top view of the cutting element of FIG. 28.
Figure 30:
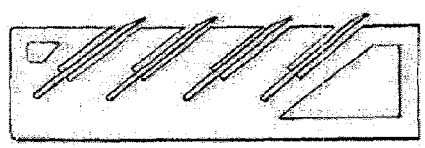
FIG. 30 shows a cross-sectional view of the cutting element of FIG. 29.

Cartilage and bone of the femoral condyles may be removed in one or more passes of a shaving element 80 as shown in FIGS. 28 through 30. The shaving element 80 is off set from the surface of the mount 81 so that a pre-determined amount of bone is shaved off of the femoral condyle with each pass or flexion of the tibia. One or more shaving elements may be supported in the base of the cutting element.

Figure 31:
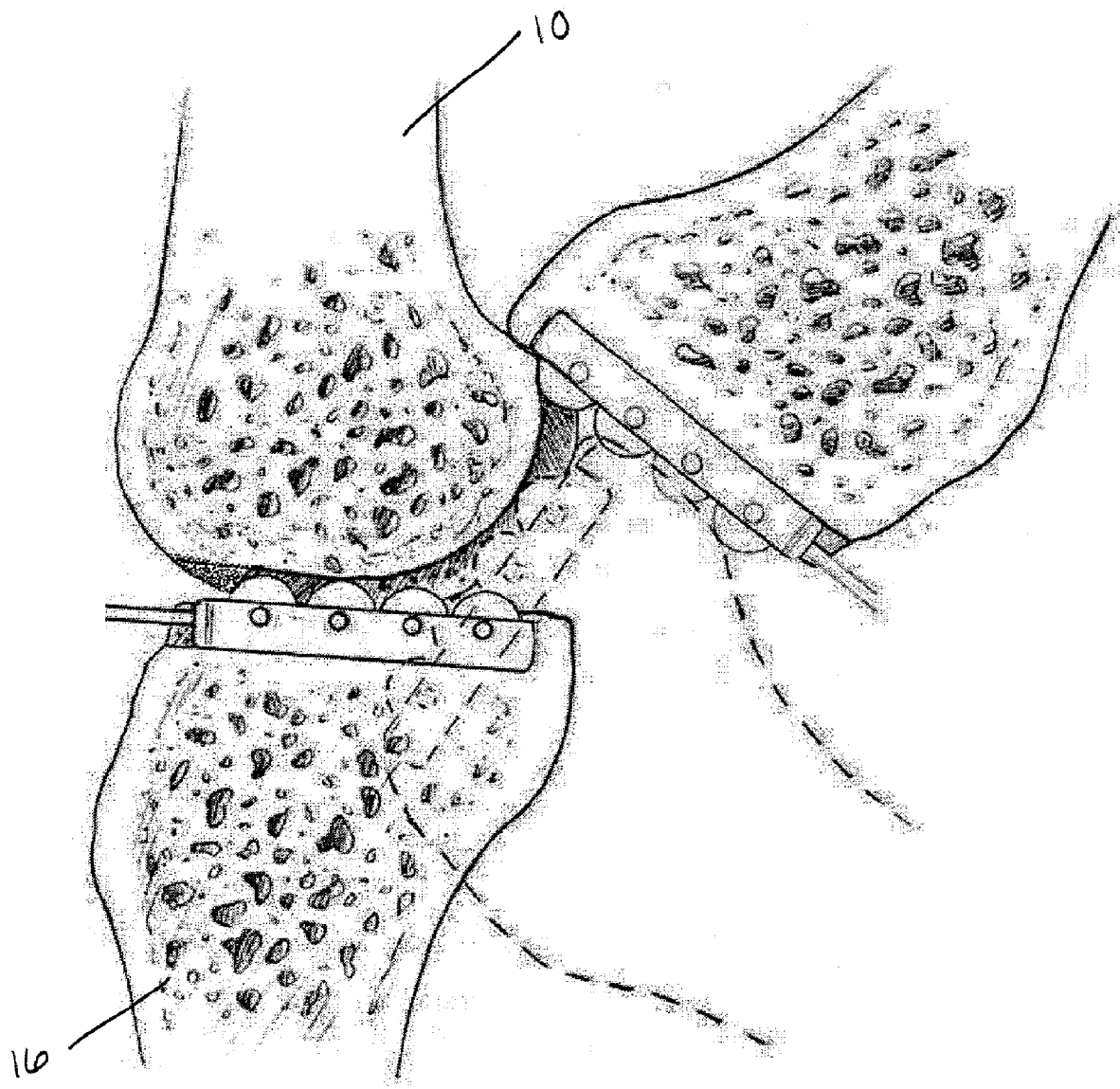
FIG. 31 illustrates the kinematics of the articulation of the knee joint in accordance with an embodiment of the present invention.

Using the instrumentation shown, articular surface of the femur may be sculpted according to the patient's individual physiology by articulating the tibia with reference to the femur. The method involves providing the apparatus having a bone sculpting tool attached to a bone mount, attaching the mount rigidly to the second bone with the tool in bone sculpting engagement with the articular surface of the first bone, and then sculpting the articular surface by articulating one of the bones with respect to the other. FIG. 31 illustrates the kinematics of the articulation of the tibia 16 about the femur 10. The bony resections of the medial and lateral femoral condyles are made by securing the cutter to the tibia and articulating the tibia. The movement of the tibia in reference to the femur follows a J-curve because of the four bar linkage of the anterior and posterior cruciate ligaments, when both are intact. In the absence of one or both cruciate ligaments, the movement of the tibia as the knee is flexed is controlled by the collateral and capsular ligaments. The bony support surface thus created in the medial and lateral femoral condyles will be shaped and positioned relative to the kinematics of the given patient.

Preoperative evaluation of patient x-rays may be used to assess deformity of the joint and appropriate spacing required to realign the joint. Additionally, spacers, for example balloons, may be used preoperatively to assess the range of motion of the joint and patient kinematics.

During the surgery appropriate spacers are placed between the bone structures to provide appropriate distraction and alignment of the joint. A distraction force provided between the femur and the tibia during the sculpting procedure may be used to account for material that has worn away from the articular surfaces. Use of a distraction force generally re-establishes normal alignment of the joint. Such spacers also tension the soft tissue structures to reduce the envelop of motion between the bone structures and increase transverse and rotational stability of the joint. The spacer may further be used to support the bone-cutting element during resection of the bone structures. Ligament releases necessary to restore appropriate limb alignment and ligament tension/balance may be performed prior to inserting the spacers.

Any one of a variety of devices may be used to maintain appropriate tension of the ligaments capsule and tendons. Such tensioning devices may include, but are not be limited to, gravity with the weight of the lower limb, intraarticular spacers, bladders, balloons, bellows, gear mechanisms, scissor mechanisms, or other expandable devices, or other elements that might engage or attach to the opposing sides of the joint. Moreover, the distraction force may be provided by an expanding base in the cutting element. A distraction device may also be useful in conjunction with a mount having skid surfaces on the shoulders. The shoulder allows the depth and shape of the femoral resection to be controlled both by the articulation of the tibia to the femur and the shape of the femur.

Specifically, for pre-operative assessment, spacers such as balloons may be provided in both the medial and the lateral resections. During surgery, a balloon may be provided in the medial resection and a spacer, for example a bellows, having a cutter attached may be provided in the lateral resection. Alternately a bellows having a cutter attached may be provided in both the lateral and the medial resections.

Figure 32:
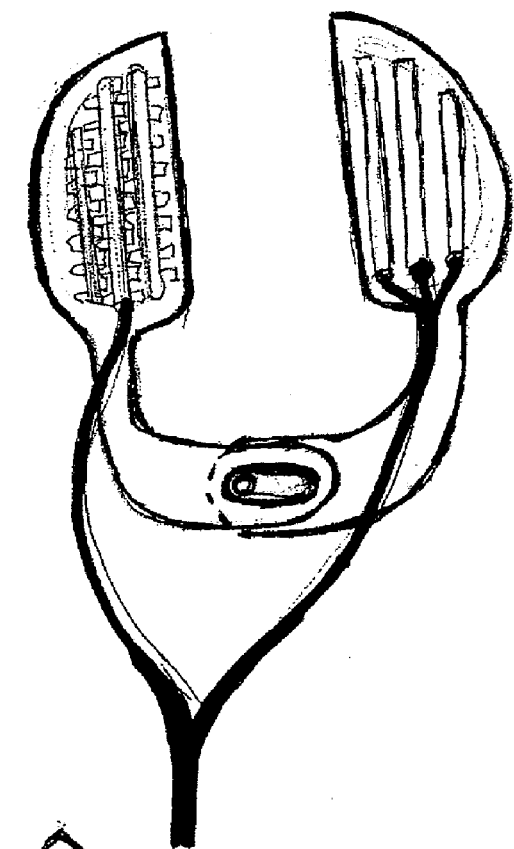
FIG. 32 shows plan view of two cutting element linked by a hinge mechanism according to an embodiment of the present invention.
Figure 33:
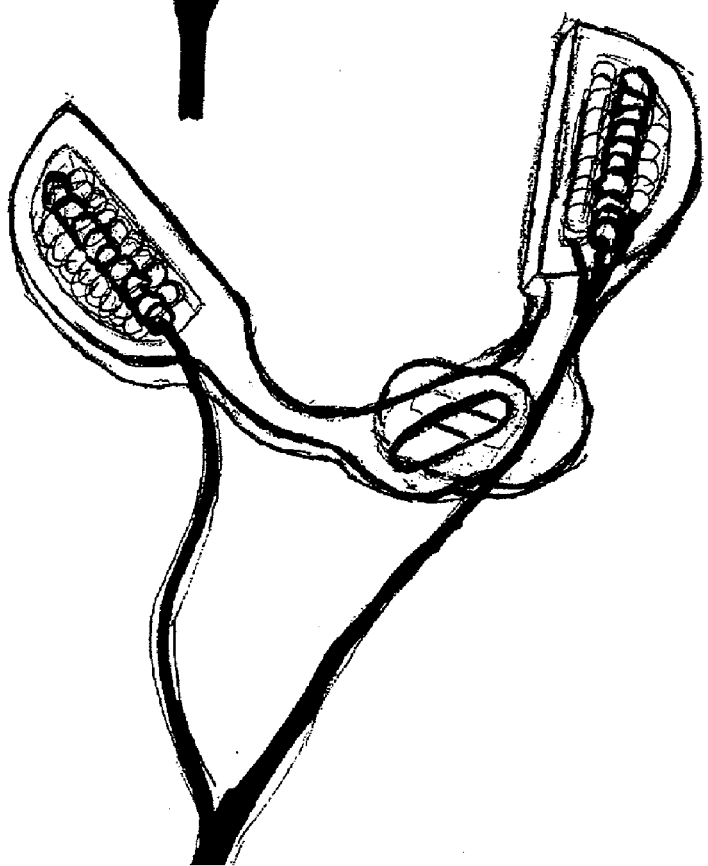
FIG. 33 shows a plan view of an alternate state of the two cutting element linked by a hinge mechanism of FIG. 31.

FIGS. 32 and 33 provide closed and open depictions, respectively, of two cutting elements 61 and 63 linked by a hinge mechanism 62 to maintain the cutting elements in a common plane while preparing the femoral condyles. The hinge mechanism 62 allows adjustability of the placement of the two cutting elements 61 and 63 in reference to one another.

Figure 34:
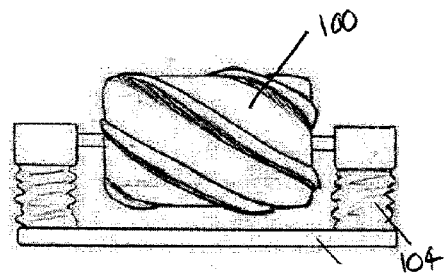
FIG. 34 shows a sectional view of a cutting element and distractor according to one embodiment of the present invention.
Figure 35:
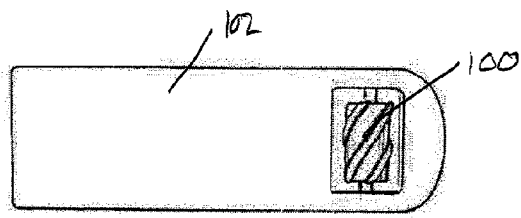
FIG. 35 shows a top view of the cutting element of FIG. 34.

FIGS. 34 and 35 provide end and side views, respectively, of a cutting element 100 supported in a platform 102 that is configured for elevation via fluid pressure applied to a distractor 104 that surrounds the cutting element 100. Applying pressure to the distractor 104 forces the milling burr into the femoral condyle to a predetermined depth as set by the top surface of the cutting element. The distractor 104 in combination with the top surface of the cutting element ensures proper resection depth while tensioning the soft tissue structures spanning the knee joint. The benefit of tensioning the soft tissue structures is to reduce the envelop of motion of the knee, stabilize the knee and provide increased accuracy and repeatability of the femoral condyle resections. An alternate embodiment may use a spacer placed between the floor of the cavity created in the tibia and the bottom of the cutting element to provide a distraction force.

Figure 36:
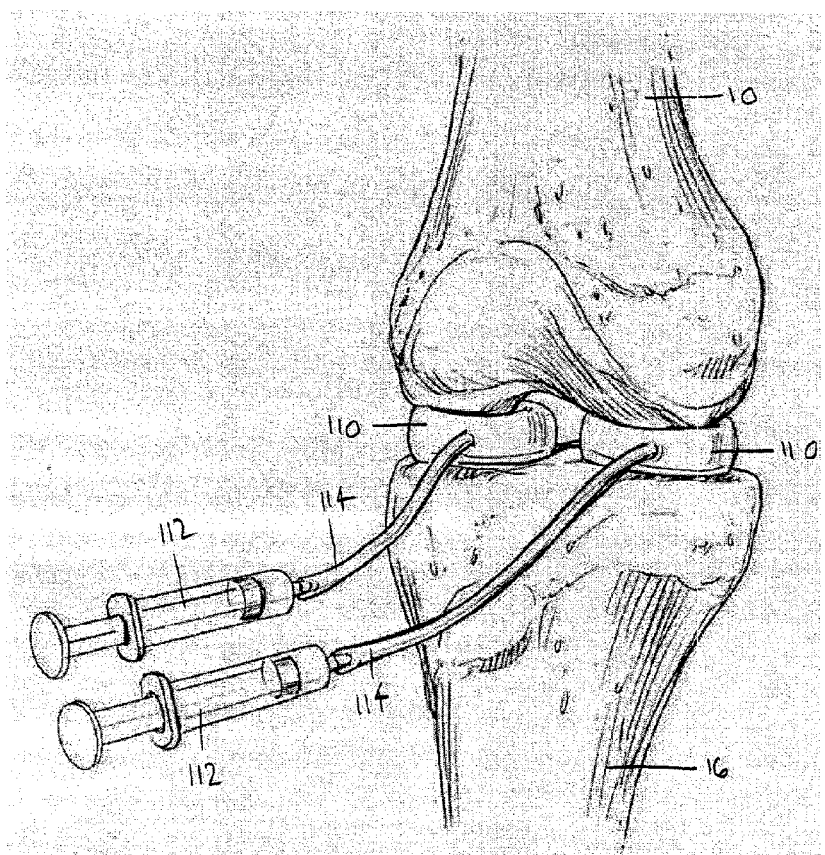
FIG. 36 shows a plan view of distractors deployed in the knee joint according to an embodiment of the present invention.

FIG. 36 shows balloon spacers 110 used to support the femoral condyles to distract the femur 10. Syringes or pumps 112 may be attached via hoses 114 to balloon spacers 110. Balloon spacers 110 are an example of an expandable spacer. Where an expandable spacer is used, pre-operative evaluation should be performed. During surgery an expandable spacer is placed between the bone structures to be resected. The cutting element may be housed in the dynamic spacer with the cutting element adjustable to the dynamic spacer to set the depth of resection. The dynamic spacer may function under load control in which case a constant distraction force is applied between the bone structures throughout a range of motion, or under displacement control. Under displacement control, a constant displacement is maintained between the bone structures throughout a range of motion. In each case, the dynamic spacer houses the cutting element and the cutting element is held at a pre-set depth relative to the bone structure being resected while the joint is flexed and extended. The dynamic spacer allows the kinematics of the joint to define the resection path in each of the bone structures.

Figure 37:
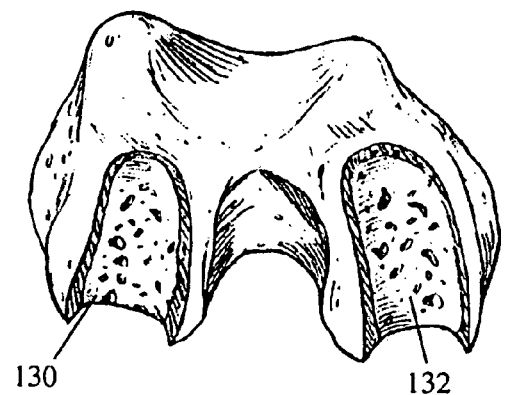
FIG. 37 shows a plan view of femoral resections made in accordance with an embodiment of the present invention.
Figure 38:
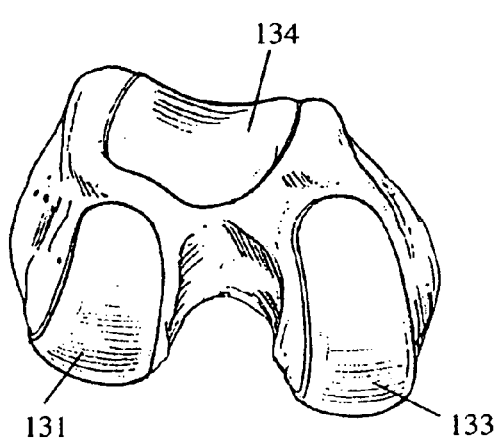
FIG. 38 shows a plan view of the femoral implants of FIG. 41 placed in the resections illustrated in FIG. 37 in accordance with an embodiment of the present invention.

As the tibia is articulated through flexion and extension, the femoral cutter prepares resections in the femoral condyles for receiving femoral components of a knee implant. FIG. 37 shows the bone resections 130 and 132. FIGS. 38, 39, 44 and 45 depict alternate embodiments of femoral implants placed in the bone resections in the femoral condyle.

Implants.

The surgical procedure is preferably performed through minimally invasive incisions that do not necessitate subluxation or dislocation of the patella. Therefore, implants such as the femoral, tibial or patellar implants are designed that may be fit through minimally invasive incisions and either oriented or joined within the joint. The femoral and tibial implants may be attached to bone with conventional bonding methods such as with, but not limited to, polymethylmethacrylate or by direct attachment to bone as with, but not limited to, a porous ingrowth surface.

The tibial baseplate is optionally configured as one piece to cover most of the prepared surface of the tibial plateau as relates to the knee. If configured as a single platform, the tibial baseplate provides a capture mechanism for a fixed bearing or a mobile bearing insert for either the medial or lateral tibiofemoral compartment. As an option a single platform is designed that provides a fixed bearing capture mechanism for the medial tibiofemoral compartment and a mobile bearing capture mechanism or a simple platform to receive a mobile bearing insert. Since right and left tibial baseplates are required, the same baseplate may be used for a mobile bearing medial insert and a fixed bearing lateral insert.

Figure 40:
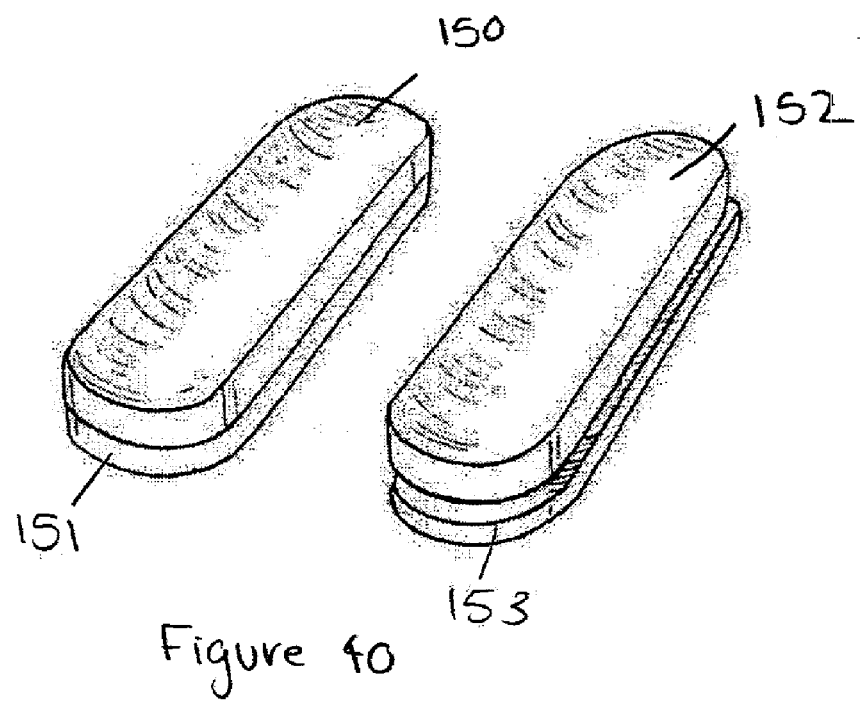
FIG. 40 shows plan views of alternate embodiments of tibial baseplates in accordance with an embodiment of the present invention.

Alternatively, as depicted in FIG. 40, the tibial implants may be configured as separate plateau baseplates for the medial and lateral compartments. These platforms might be oriented one to the other by an alignment instrument that dictates the orientation in relationship to each other and/or to the femoral components. The tibial baseplates may be fixed bearing and manufactured completely of polyethylene. Thus, fixed bearing tibial components 150 with a metal support tray 151, and mobile bearing tibial components 152 with metal support tray 153 may be used in the same knee replacement surgery. Furthermore, the tibial baseplate may accommodate separate fixed and mobile bearing inserts in either or both medial and lateral compartments.

Figure 41:
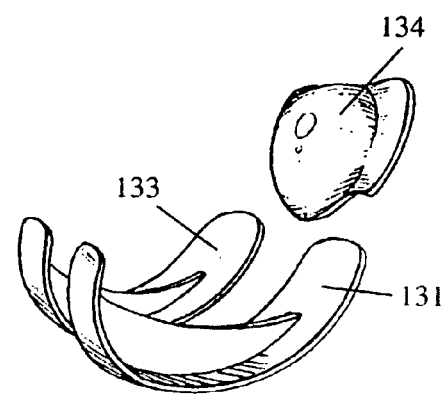
FIG. 41 shows a plan view of femoral implants for resurfacing the femoral resections of FIG. 38 according to an embodiment of the present invention.

It is preferable to place all of the implants through small incisions. As seen in FIG. 41, the femoral implants include a first component 131 to resurface the articulating surface of the medial condyle and a second component 133 to resurface the articulating surface of the lateral condyle. An optional third component 134 may be provided to resurface the femoral side of the patellofemoral joint. Optionally, the femoral component(s) may include a fin along its support or convex internal surface for upward driven implantation. The fin may be shaped as a web extending from one portion of the internal surface to another.

Figure 39:
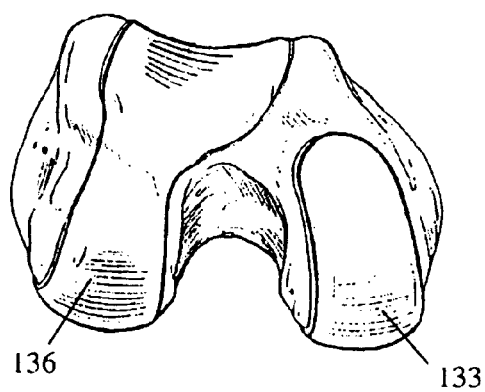
FIG. 39 show a plan view of the femoral implants of FIG. 42 placed in the resections illustrated in FIG. 37 in accordance with an embodiment of the present invention.
Figure 42:
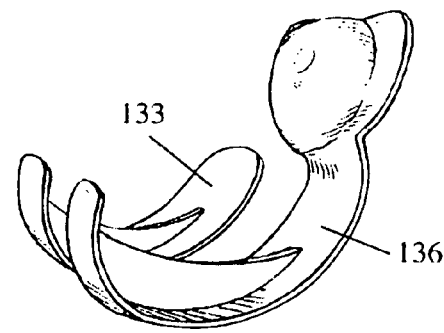
FIG. 42 shows a plan view of femoral implants for resurfacing the femoral resections of FIG. 40 according to an embodiment of the present invention.
Figure 45:
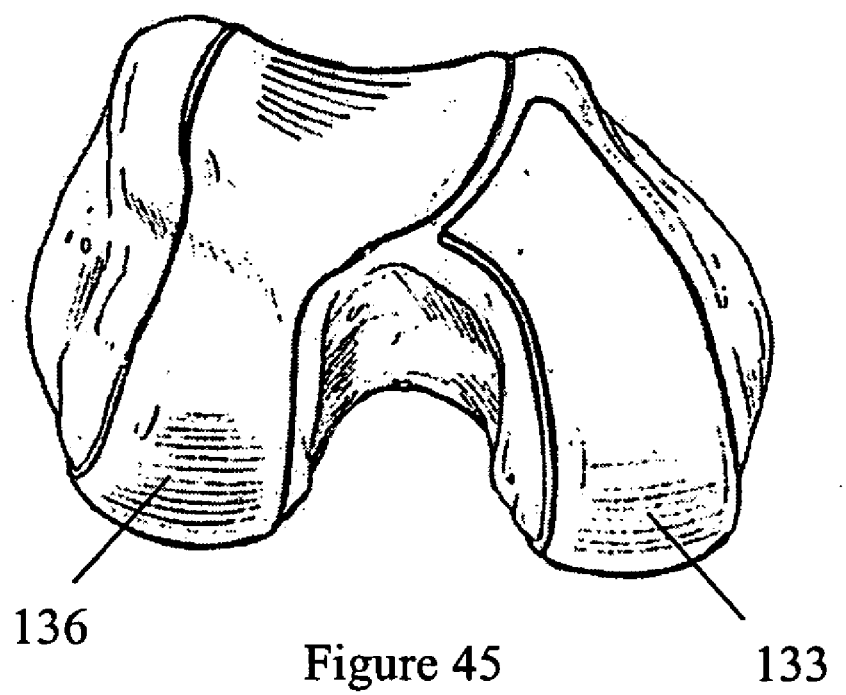
FIG. 45 shows a plan view of a plurality of components placed in the resections illustrated in FIG. 37 in accordance with the present invention.

As shown in FIGS. 39 and 45 the lateral femoral implant may be continuous with the patellar flange forming a unitary piece 136 that may be passed through a small incision. To accommodate the continuous piece, the lateral condylar component and the patellofemoral component optionally may be a single component 133 extending from the top of the patellofemoral groove and extending over the lateral condyle both distally and posteriorly, as seen in FIGS. 39 and 45. FIG. 42 provides a side view of a femoral implant combining the lateral condylar component and the patellofemoral component into a single component 136.

The bearing elements may be manufactured of ultra high molecular weight polyethylene but may also be manufactured of any suitable biocompatible material as known in the art. The bearing elements generally include three compartments: medial tibial condyle, lateral tibial condyle and patella. Preferably, a choice of bearing elements is provided for either fixed or mobile bearing of each compartment. Thus, for example, the surgeon would have at his discretion inserting either a mobile bearing or a fixed bearing insert into each of the tibial components, one medial and one lateral.

The convex surface of the femoral condyle is the bearing surface and interacts with the tibial bearing implants. Optionally, the femoral component(s) may include a fin along its convex internal surface for upward driven implantation. The fin may be shaped as a web extending from one portion of the internal surface to another.

The femoral components may include an alignment device to orient separate femoral components in relationship to one another and/or to the tibial components.

The femoral components are provided in a variety of sizes and optionally include components that are flexible to provide optimum fit for minor variations in the shape of the prepared femoral condyles.

Figure 43:
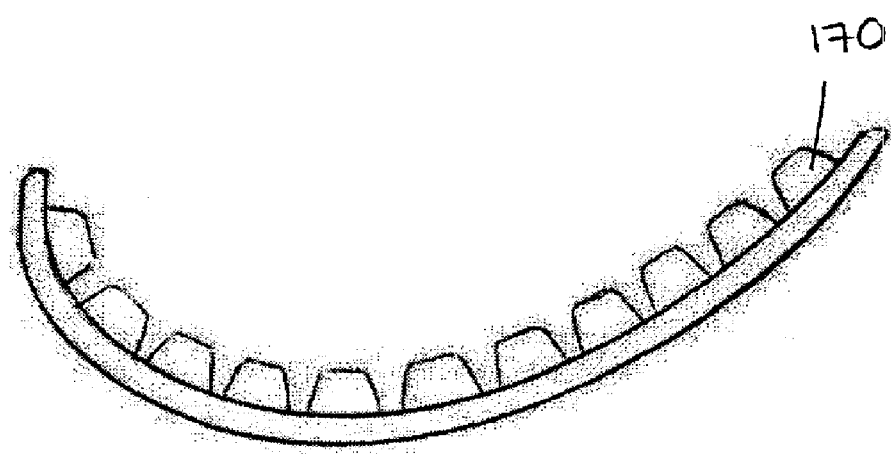
FIG. 43 shows a plan view of a femoral implant in accordance with an embodiment of the present invention.
Figure 44:
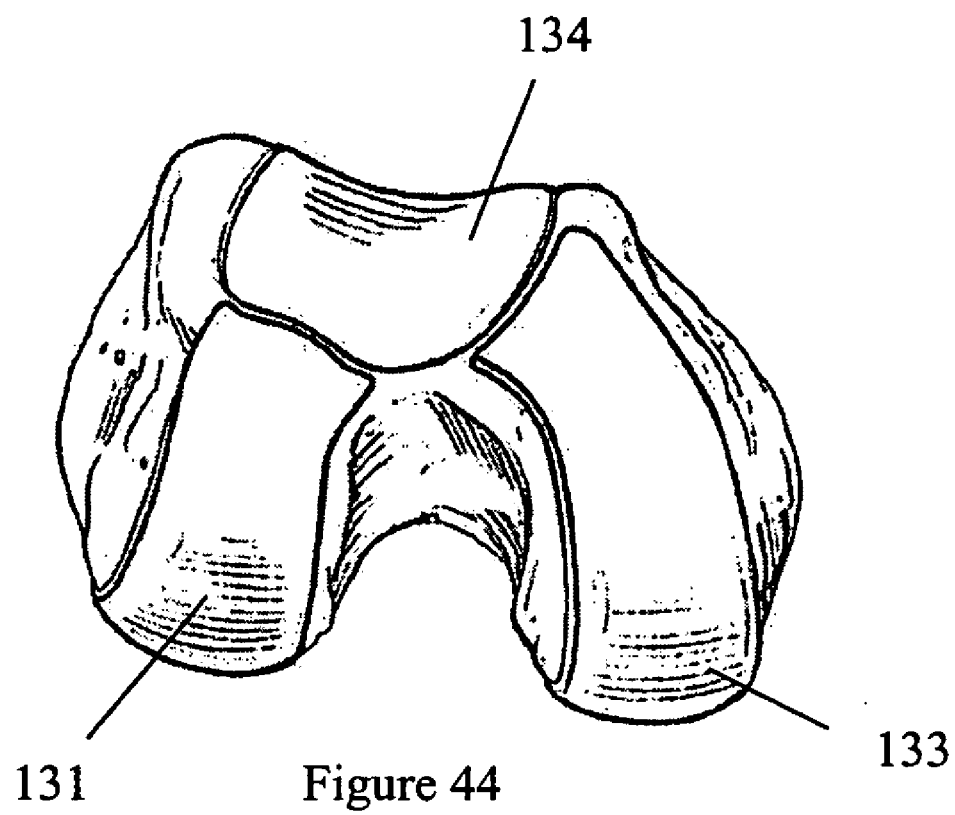
FIG. 44 shows a plan view of a plurality of components placed in the resections illustrate in FIG. 37 in accordance with present invention.

FIG. 43 is an illustration of an optional embodiment of the femoral condyle implants configured as flexible implants. The outer surface of the femoral condyle implant is a thin sheet of metal forming an articular surface preferable of cobalt chromium alloy. Other suitable implant grade alloys, polymers, or metals, for example, stainless steel, titanium alloy, or Nitinol, may be used. In order to provide uniform deflection in one plane, the implant is thin and of uniform cross section. The support surface of the femoral condyle implant is lined with molded bone cement, such as polymethylmethacrylate (PMMA or PMA), spacers that are bonded to the articular surface. The spacers may be shaped as blocks or any other configuration suitable for molding in place during fabrication. Generally, the spacers are shaped to span the femoral condyle implant from side to side, in a coronal plane, while providing spaces between spacers at given intervals to facilitate mild flexing of the articular surface. Such flexing enables the flexible femoral condyle to conform to the unique shape of the prepared bony support surface in the femoral condyle, thereby taking full advantage of the kinematicly defined support surface. Such implants are provided in a range of sizes to accommodate individual patient physiology and to minimize the amount of flexing a given implant may make in conforming to the prepared surface. Hence, the distortion of the articular surface is minimal.

In use, the resected femoral condyle is covered with doughy bone cement. The femoral implant is placed and loaded against the resected femoral condyle until the bone cement cures.

The preferred method for preparing the femoral condyle uses the tibia as a support for the milling cutter. The soft tissue structures of the knee provide the path of motion to move the cutter through the femoral condyle. The kinematics of the knee are well understood and defined. This approach necessarily results in a unique shape machined into each femoral condyle due to variations in soft tissue structures and bony structures from patient to patient.

In an alternate embodiment, the femoral condyles may be ridged and of given size. Each implant is composed of a plurality of components 170. Components 170 are cemented in place with bone cement, which acts as a grouting material to fill the space between the implant and the supporting bone. Bone cement has been shown to provide long term implant stability when applied in thickness up to two mm. Hence, a range of implant sizes covers the range of femoral condyle sizes anticipated and the variation in shape anticipated.

While a preferred embodiment of the present invention has been described, it should be understood that various changes, adaptations and modifications may be made therein without departing from the spirit of the invention and the scope of the appended claims.

The invention claimed is:

1. An apparatus for replacing the surfaces of a joint between a first bone and a second bone, the first bone articulating in a predetermined manner with a second bone, the apparatus comprising:

a first bone implant including a plurality of individual components for mimicking and replacing the bearing surface of the first bone, each of said plurality of individual components having an inner surface adapted to be secured to the first bone and an outer surface; and a second bone implant for mimicking and replacing respective bearing surfaces of the second bone; wherein the outer surface of said plurality of individual components of the first bone implant contacts said second bone implant and further wherein each of said plurality of individual components of the first bone implant are structured to be aligned, oriented and engaged one to the other within the confines of the joint cavity during surgical placement therewithin and the resulting configuration of the first bone implant and second bone implant articulate in a predetermined manner to restore proper kinematics; and further wherein the material used to construct the plurality of individual components of the first bone implant is of a similar material.

2. The apparatus of claim 1 wherein the components of the first bone implant and the second bone implant are aligned and oriented to each other within the confines of the joint cavity during surgical placement therewithin.

3. The apparatus of claim 1 wherein the second bone implant is configured as a unitary piece.

4. The apparatus of claim 1 wherein the second bone implant further comprises a fixed bearing attachment and a bearing attached thereto, and a mobile bearing attachment and a bearing attached thereto.

5. The apparatus of claim 1 wherein the second bone implant further comprises a plurality of components.

6. The apparatus of claim 5 wherein at least one of the second bone components is fixed bearing.

7. The apparatus of claim 5 wherein at least one of the second bone components is mobile bearing.

8. The apparatus of claim 5 wherein the second bone components are a combination of fixed bearing and mobile bearing components.

9. The apparatus of claim 1 wherein the first bone implant comprises two bearing-surface components.

10. The apparatus of claim 1 wherein the first bone implant comprises three bearing-surface components.

11. The apparatus of claim 1 wherein each of the plurality of individual components of the first bone implant further comprises a fin longitudinally disposed along an axis of said each of said plurality of individual components for driving the components into the first bone.

12. The apparatus of claim 1 wherein the first bone implant is a femoral implant and the second bone implant is a tibial implant.

13. The apparatus of claim 1 wherein the first bone implant and second bone implant are each sized for insertion through a minimally invasive incision.

14. The apparatus of claim 1 wherein the plurality of individual components of the first bone implant are flexible components.

15. The apparatus of claim 1 wherein the plurality of individual components of the first bone implant are rigid components.

16. The apparatus of claim 1 wherein the plurality of individual components of the first bone implant are a combination of rigid components and flexible components.

17. An apparatus for replacing the surfaces of a joint between a first bone and a second bone, the first bone normally articulating in a predetermined manner with a second bone, the apparatus comprising a first bone implant including a plurality of individual components for mimicking and replacing the bearing surface of the first bone, each of said plurality of individual components having an inner surface and an outer surface, the inner surface adapted to be secured to the first bone and including a plurality of spacers thereon; and a second bone implant for mimicking and replacing the bearing surface of the second bone; wherein the outer surface of said plurality of individual components of said first bone implant contacts the second bone implant, and further wherein the components of the first bone implant are joined within the confines of the joint cavity during surgical placement therewithin and the first bone implant and the second bone implant articulate in a predetermined manner.

18. The apparatus of claim 17 further including a hardenable fluid for cementing the spacers.

19. The apparatus of claim 17 wherein the first bone implant and second bone implant are each sized for insertion through a minimally invasive incision.

20. The apparatus of claim 17 wherein the plurality of individual components of the first bone implant are flexible components.

21. The apparatus of claim 17 wherein the plurality of individual components of the first bone implant are rigid components.

22. The apparatus of claim 17 wherein the plurality of individual components of the first bone implant are a combination of rigid components and flexible components.

23. A method of replacing the articular surfaces of a first bone that normally articulates in a predetermined manner with a second bone and replacing the articular surfaces of the second bone, comprising:
   a) resecting a portion of the second bone to provide the second bone with a resected cavity;
   b) providing an apparatus comprising a bone-sculpting tool attached to a bone mount;
   c) attaching the mount rigidly in the cavity;
   d) sculpting the articular surfaces of the first bone by articulating one of the bones with respect to the other;
   e) providing a first bone implant comprising a plurality of individual components and a second bone implant;
   f) placing the components of the first bone in the first bone resections;
   g) placing the second bone implant in the second bone resection; and
   h) joining the components of the first bone implant and the second bone implant within the confines of the joint cavity.

24. The method of claim 23 wherein the step of joining further comprises aligning and orienting the components of the first bone implant and the second bone implant within the confines of the joint cavity.

25. The method of claim 23 further comprising the step of adjusting the position and orientation of the tool to bring the tool into bone-sculpting engagement with the articular surface of the first bone.

26. The method of claim 23 wherein the second bone resection is formed by advancing a cutting mill into the second bone.

27. The method of claim 23 wherein the femoral implant comprises a first component for resurfacing the medial condyle and a second component for resurfacing the lateral condyle.

28. The method of claim 27 wherein the second component also resurfaces the patellofemoral groove.

29. The method of claim 23 wherein the femoral implant comprises a first component for resurfacing the medial condyle, a second component for resurfacing the lateral condyle and a third component for resurfacing the patellofemoral groove.

30. The method of claim 23 wherein fins are provided centrally on each component of the femoral implant for support.

31. The method of claim 23 wherein each component further comprises a fin for driving into the femur for implantation.

32. The method of claim 23 wherein each component has an inner surface and an outer surface and wherein the inner surface is comprised of a plurality of spacers.

33. The method of claim 32 wherein the a plurality of segments are bonded to an articular surface.

34. The method of claim 32 wherein the outer surface is a thin sheet of implant grade material.

35. The method of claim 32 wherein the each component is coated with a hardenable fluid.

36. An apparatus for replacing the surfaces of a femur and a tibia, where the tibia normally articulates in a predetermined manner with the femur, the apparatus comprising:
   a femoral implant including a plurality of individual components sized for insertion through a minimally invasive incision, each of said plurality of individual components having an inner surface and an outer surface, the inner surface adapted to be secured to the femur; and
   a tibial implant including a plurality of individual components sized for insertion through a minimally invasive incision;
   wherein the outer surface of said plurality of individual components of the femoral implant contact the tibial implant; and further wherein each of the plurality of individual components of the femoral implant are structured to be aligned, oriented and joined one to the other within the confines of the joint cavity during surgical placement therewithin, and each of the plurality of individual components of the tibial implant are structured to be aligned, oriented and joined to each other within the confines of the joint cavity during surgical placement therewithin, and the femoral implant and tibial implant articulate in a predetermined manner to restore proper kinematics.

37. The apparatus of claim 36 wherein the tibial implant comprises separate tibial components for the medial and lateral compartments of the tibia.

38. The apparatus of claim 36 wherein at least one of the tibial implant components is fixed bearing.

39. The apparatus of claim 36 wherein at least one of the tibial implant components is mobile bearing.

40. The apparatus of claim 37 wherein the tibial implant components are a combination of fixed bearing and mobile bearing.

41. The apparatus of claim 36 wherein the plurality of individual components of the femoral implant are flexible components.

42. The apparatus of claim 36 wherein the plurality of individual components of the femoral implant are rigid components.

43. The apparatus of claim 36 wherein the plurality of individual components of the femoral implant are a combination of rigid components and flexible components.

44. An apparatus for replacing the articulating surfaces of a femur and a tibia, where the tibia normally articulates in a predetermined manner with a femur, the apparatus comprising:
   a femoral implant including a plurality of individual components sized for insertion through a minimally invasive incision each of said plurality of individual components having an inner surface adapted to be secured to the femur and an outer surface; and a tibial implant comprising a plurality of individual components sized for insertion through a minimally invasive incision, the tibial implant components comprising a fixed bearing attachment and a bearing attached thereto, and a mobile bearing attachment and a bearing attached thereto;

wherein the outer surface of said plurality of individual components of the femoral implant contact the tibial implant; and further wherein each of said plurality of individual components of said femoral implant are structured to be aligned, oriented and engaged one to the other within the confines of the joint cavity during surgical placement therewithin, and the components of the tibial implant are structured to be aligned, oriented and engaged one to the other within the confines of the joint cavity during surgical placement therewithin; and further wherein the resulting femoral implant and the tibial implant articulate in a predetermined manner to restore proper kinematics.

45. The apparatus of claim 44 wherein the plurality of individual components of the femoral implant are flexible components.

46. The apparatus of claim 44 wherein the plurality of individual components of the femoral implant are rigid components.

47. The apparatus of claim 44 wherein the plurality of individual components of the femoral implant are a combination of rigid components and flexible components.

48. A method of replacing the articular surfaces of a first bone that normally articulates in a predetermined manner with a second bone and replacing the articular surfaces of the first bone, comprising:
  a) resecting a portion of the second bone to provide a second bone resection;
  b) providing an apparatus comprising a bone-sculpting tool attached to a bone mount;
  c) attaching the mount rigidly to the second bone resection;
  d) sculpting the articular surface to provide first bone resections of the first bone by articulating one of the bones with respect to the other;
  e) providing a hardenable fluid along the sculpted surface;
  f) providing a first bone implant comprising a plurality of individual components wherein each component has an inner surface and an outer surface and wherein the inner surface is comprised of a plurality of spacers;
  g) providing a second bone implant;
  h) placing the components of the first bone in the first bone resections;
  i) allowing the hardenable fluid to cure;
  j) placing the second bone implant in the second bone resection; and
  k) joining the components of the first bone implant within the confines of the joint cavity and joining the components of the second bone implant within the confines of the joint cavity.

49. The method of claim 48 further including articulating the second bone with respect to the first bone such that the second bone implant moulds the plurality of spacers along the shape of the resected surface.

50. An apparatus for partially replacing the surfaces of a femur, the apparatus comprising a plurality of individual bearing-surface components sized for insertion through a minimally invasive incision, said plurality of individual bearing-surface components having an inner surface adapted to be secured to the femur and an outer surface adapted to contact a second bone implant; wherein each of the plurality of individual bearing-surface components are structured to be individually placed into the joint cavity, and structured to be aligned, oriented and joined one to the other within the confines of the joint cavity during surgical placement therewithin to restore proper kinematics; and further wherein the material used to construct the plurality of individual bearing-surface components is of a similar material.

51. The apparatus of claim 50 wherein the plurality of bearing-surface components replace a medial and lateral femoral condyle.

52. The apparatus of claim 50 wherein the plurality of bearing-surface components replace a patellofemoral groove and lateral femoral condyle.

53. The apparatus of claim 50 wherein the plurality of bearing-surface components replace a patellofemoral groove and a medial femoral condyle.

54. The apparatus of claim 50 wherein the plurality of individual bearing-surface components are flexible components.

55. The apparatus of claim 50 wherein the plurality of individual bearing-surface components are rigid components.

56. The apparatus of claim 50 wherein the plurality of individual bearing-surface components are a combination of rigid components and flexible components.

57. An apparatus for partially replacing the surfaces of a femur, the apparatus comprising a plurality of individual bearing-surface components sized for insertion through a minimally invasive incision wherein the plurality of individual bearing-surface components have an inner surface adapted to be secured to the femur and an outer surface adapted to contact a second bone implant, and further wherein each of the plurality of individual bearing-surface components are designed to be individually placed into the joint cavity and structured to be aligned, oriented and engaged one to the other within the confines of the joint cavity during surgical placement therewithin to restore proper kinematics; and further wherein the material used to construct the plurality of individual bearing-surface components is of a similar material.

58. The apparatus of claim 57 wherein the plurality of bearing-surface components replace a medial and lateral femoral condyle of the femur.

59. The apparatus of claim 57 wherein the plurality of bearing-surface components replace a patellofemoral groove and lateral femoral condyle of the femur.

60. The apparatus of claim 57 wherein the plurality of bearing-surface components replace a patellofemoral groove and medial femoral condyle of the femur.

61. The apparatus of claim 57 wherein the plurality of individual bearing-surface components are flexible components.

62. The apparatus of claim 57 wherein the plurality of individual bearing-surface components are rigid components.

63. The apparatus of claim 57 wherein the plurality of individual bearing-surface components are a combination of rigid components and flexible components.

64. A bicompartmental prosthesis configured for implantation within a joint cavity comprising medial tibial and medial femoral components and lateral tibial and lateral femoral components, each of said components having an inner surface and an outer surface, wherein the inner surface of said medial femoral component and lateral femoral component are adapted to be secured to a femur and the inner surface of said medial tibial component and said lateral tibial component are adapted to be secured to a tibia, and further wherein the outer surface of said medial femoral component and lateral femoral component contact the outer surface of said medial tibial and lateral tibial components, and further wherein the medial femoral component and lateral femoral component are structured to be individually placed into the joint cavity, and structured to be aligned, oriented and joined one to the other within the confines of the joint cavity during surgical placement therewithin to restore proper kinematics and the medial tibial component and lateral tibial component are designed to be individually placed into the joint cavity, and structured to be aligned, oriented and joined one to the other within the confines of the joint cavity during surgical placement therewithin to restore proper kinematics.

65. The bicompartmental prosthesis of claim 64 wherein the medial femoral and lateral femoral components are flexible components.

66. The bicompartmental prosthesis of claim 64 wherein the medial femoral and lateral femoral components are rigid components.

67. The bicompartmental prosthesis of claim 64 wherein the medial femoral and lateral femoral components are a combination of rigid components and flexible components.

68. A bicompartmental prosthesis for implantation within a joint cavity comprising medial tibial and medial femoral components and lateral tibial and lateral femoral components, each of said components having an inner surface and an outer surface, wherein the inner surface of said medial femoral component and lateral femoral component are adapted to be secured to a femur and the inner surface of said medial tibial component and said lateral tibial component are adapted to be secured to a tibia, and further wherein the outer surface of said medial femoral component and lateral femoral component contact the outer surface of said medial tibial and lateral tibial components, and further wherein the medial femoral component and lateral femoral component are structured to be individually placed into the joint cavity, and structured to be aligned, oriented, and engaged one to the other within the confines of the joint cavity during surgical placement therewithin to restore proper kinematics and the medial tibial component and lateral tibial component are designed to be individually placed into the joint cavity, and structured to be aligned, oriented and engaged one to the other within the confines of the joint cavity during surgical placement therewithin to restore proper kinematics.

69. The bicompartmental prosthesis of claim 68 wherein the medial femoral and lateral femoral components are flexible components.

70. The bicompartmental prosthesis of claim 68 wherein the medial femoral and lateral femoral components are rigid components.

71. The bicompartmental prosthesis of claim 68 wherein the medial femoral and lateral femoral components are a combination of rigid components and flexible components.

72. An apparatus for replacing the bearing-surface of a first bone comprising a plurality of individual bearing-surface first bone components sized for insertion through a minimally invasive incision and including an inner surface adapted to be secured to said first bone and an outer surface adapted to contact a second bone implant, wherein each of the individual bearing-surface first bone components are structured to be individually placed into the joint cavity, and structured to be aligned and oriented one to the other within the joint cavity during surgical placement therewithin to restore proper kinematics; and further wherein the material used to construct the plurality of individual bearing-surface first bone components is of a similar material.

73. The apparatus of claim 72 wherein the first bone components are femoral components.

74. The apparatus of claim 73 wherein the femoral components are joined within the confines of the joint cavity during surgical placement therewithin.

75. The apparatus of claim 73 wherein the femoral components are engaged within the confines of the joint cavity during surgical placement therewithin.

76. The apparatus of claim 72 wherein the plurality of individual bearing-surface first bone components are flexible components.

77. The apparatus of claim 72 wherein the plurality of individual bearing-surface first bone components are rigid components.

78. The apparatus of claim 72 wherein the plurality of individual bearing-surface first bone components are a combination of rigid components and flexible components.

* * * * *

UNITED STATES PATENT AND TRADEMARK OFFICE
CERTIFICATE OF CORRECTION

PATENT NO. : 7,115,131 B2 Page 1 of 1
APPLICATION NO. : 10/159147
DATED : October 3, 2006
INVENTOR(S) : Engh et al.

It is certified that error appears in the above-identified patent and that said Letters Patent is hereby corrected as shown below:

At Col. 14, Line 31, please delete "131" and insert --133--.

At Col. 14, Line 32, please delete "133" and insert --131--.

At Col. 14, Line 45, please delete "133" and insert --136--.

Signed and Sealed this

Twenty-sixth Day of June, 2007

JON W. DUDAS
*Director of the United States Patent and Trademark Office*